US008168132B2

(12) United States Patent
Zwingenberger et al.

(10) Patent No.: US 8,168,132 B2
(45) Date of Patent: May 1, 2012

(54) APPARATUS AND METHOD FOR DRYING INSTRUMENTS USING SUPERHEATED STEAM

(75) Inventors: Arthur Zwingenberger, Lucerne (CH); Gabriel Gheorghe Naghi, Ontario (CA); David Bryant Snaith, Ontario (CA); Jeffrey G. Dayman, Ontario (CA); Andy Kwan-Leung Sun, Ontario (CA); Michel Stanier, Ontario (CA)

(73) Assignee: SciCan Ltd., Toronto, Ontario (CA)

( * ) Notice: Subject to any disclaimer, the term of this patent is extended or adjusted under 35 U.S.C. 154(b) by 442 days.

(21) Appl. No.: 12/309,075

(22) PCT Filed: Jul. 6, 2007

(86) PCT No.: PCT/CA2007/001197
§ 371 (c)(1),
(2), (4) Date: Jan. 6, 2009

(87) PCT Pub. No.: WO2008/003177
PCT Pub. Date: Jan. 10, 2008

(65) Prior Publication Data
US 2009/0311135 A1    Dec. 17, 2009

(51) Int. Cl.
*A61L 2/00* (2006.01)
*A61L 2/08* (2006.01)
(52) U.S. Cl. .......................................... 422/293; 422/26
(58) Field of Classification Search .................. 422/293, 422/26
See application file for complete search history.

(56) References Cited

U.S. PATENT DOCUMENTS

| 1,377,725 | A | | 5/1921 | Pentz |
| 1,902,625 | A | | 3/1933 | Dunham et al. |
| 3,015,893 | A | | 1/1962 | McCreary |
| 3,564,723 | A | | 2/1971 | Passey et al. |
| 3,564,726 | A | | 2/1971 | Nociti et al. |
| 3,814,901 | A | * | 6/1974 | Morhack ....................... 219/401 |
| 4,121,350 | A | | 10/1978 | Buchholz |
| 4,808,377 | A | | 2/1989 | Childers et al. |
| 5,016,361 | A | | 5/1991 | Durr et al. |
| 5,290,511 | A | | 3/1994 | Newman |
| 5,519,948 | A | | 5/1996 | Raehse et al. |
| 5,735,061 | A | | 4/1998 | Lawrence |
| 6,026,588 | A | | 2/2000 | Clark et al. |
| 6,231,684 | B1 | | 5/2001 | Mouser et al. |
| 6,646,241 | B1 | | 11/2003 | Varma et al. |
| 7,079,759 | B2 | | 7/2006 | Tokutake et al. |
| 2003/0095891 | A1 | * | 5/2003 | O'Neal ........................... 422/26 |

FOREIGN PATENT DOCUMENTS

| CN | 87101549 A | 11/1987 |
| GB | 6523 A | 3/1915 |
| GB | 1026616 A | 4/1966 |
| GB | 1169248 A | 10/1969 |

(Continued)

*Primary Examiner* — Kevin Joyner
(74) *Attorney, Agent, or Firm* — Clark & Brody

(57) ABSTRACT

An apparatus and method for drying instruments using superheated steam is disclosed. The apparatus comprises a chamber for receiving the instruments, a distribution means for distributing superheated steam within the chamber and an exhaust means for purging vaporized moisture from the chamber. The chamber has at least one inlet port which is connected to the distribution means. The method comprises sterilizing the instruments using saturated steam generated by the steam generation means and drying the instruments using superheated steam generated by the steam generation means to vaporize moisture within the chamber and purging the vaporized moisture from the chamber using the exhaust means.

19 Claims, 22 Drawing Sheets

FOREIGN PATENT DOCUMENTS

| | | |
|---|---|---|
| JP | 03-207366 | 9/1991 |
| JP | 09-206360 | 8/1997 |
| JP | 3596144 | 8/1997 |
| JP | 09-285527 | 11/1997 |
| JP | 2000-097498 | 4/2000 |
| JP | 2000-161786 | 6/2000 |
| JP | 2001-187118 | 7/2001 |
| JP | 2001-190642 | 7/2001 |
| JP | 2002-011077 | 1/2002 |
| JP | 2002-017825 | 1/2002 |
| JP | 2002-022101 | 1/2002 |
| JP | 2002-35090 | 2/2002 |
| JP | 2002-052070 | 2/2002 |
| JP | 2002-065816 | 3/2002 |
| JP | 2002-085528 | 3/2002 |
| JP | 2002-102316 | 4/2002 |
| JP | 2002-224198 | 8/2002 |
| JP | 2002-325825 | 11/2002 |
| JP | 2003-004204 | 1/2003 |
| JP | 2003-074801 | 3/2003 |
| JP | 2003-205019 | 7/2003 |
| JP | 2004-089563 | 3/2004 |
| JP | 2004-332956 | 11/2004 |
| JP | 2005-065991 | 3/2005 |
| JP | 2005-230429 | 9/2005 |
| JP | 2006-105523 | 4/2006 |
| WO | WO 2004/005798 | 1/2004 |

* cited by examiner

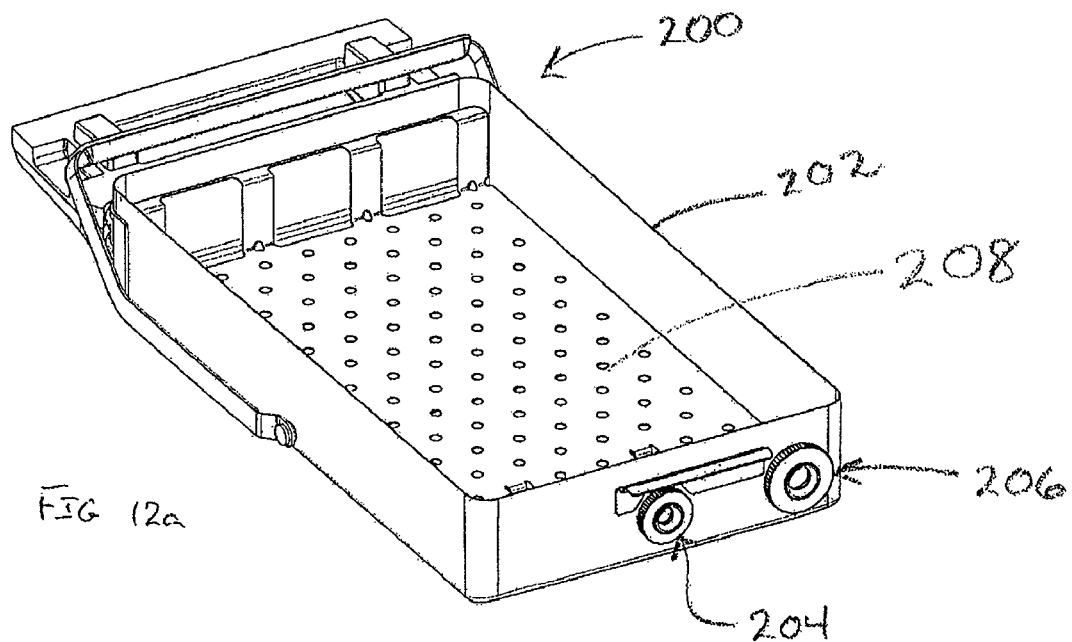
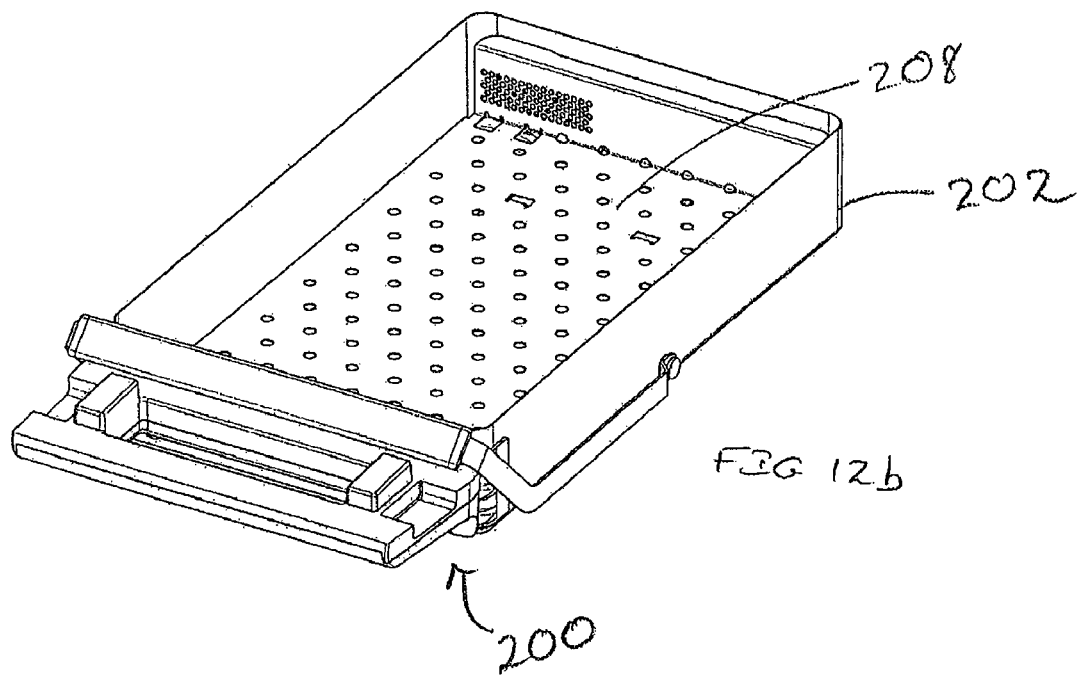

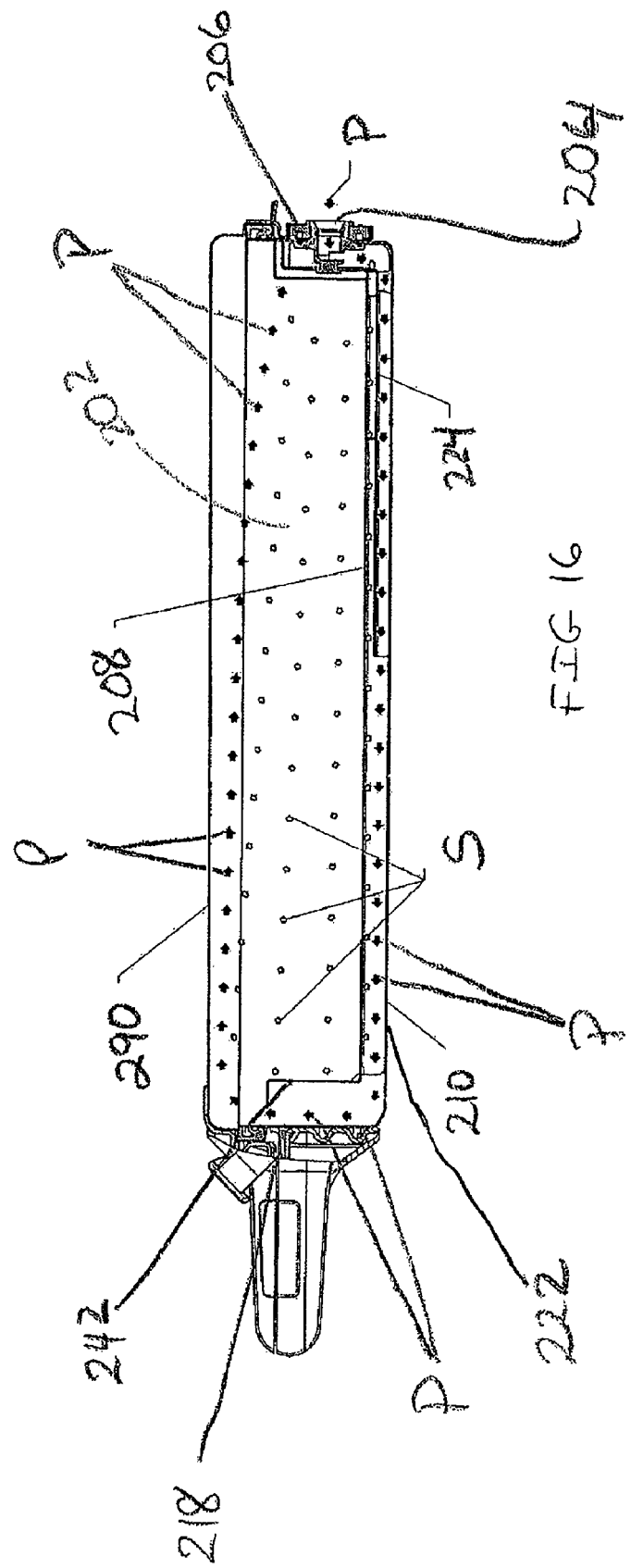

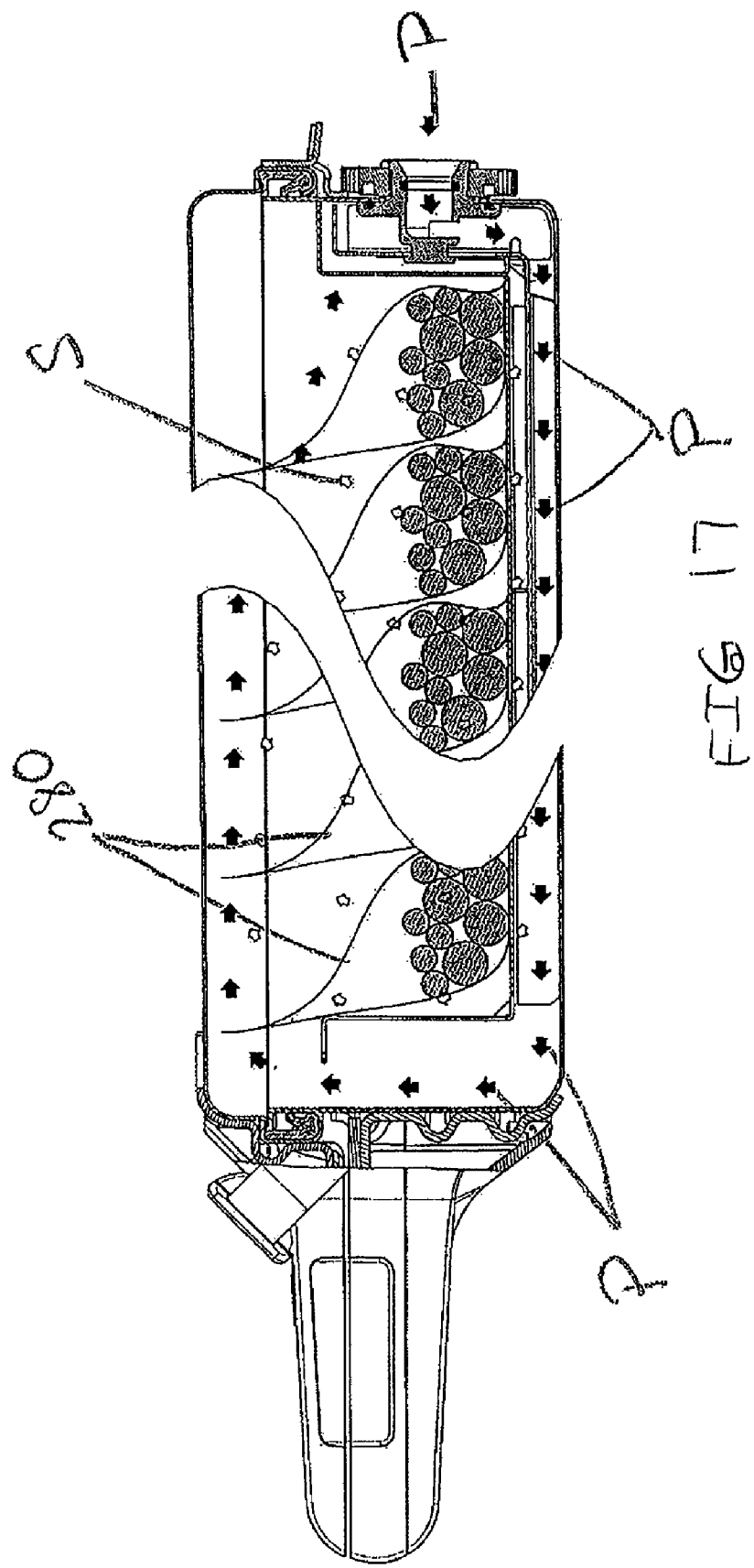

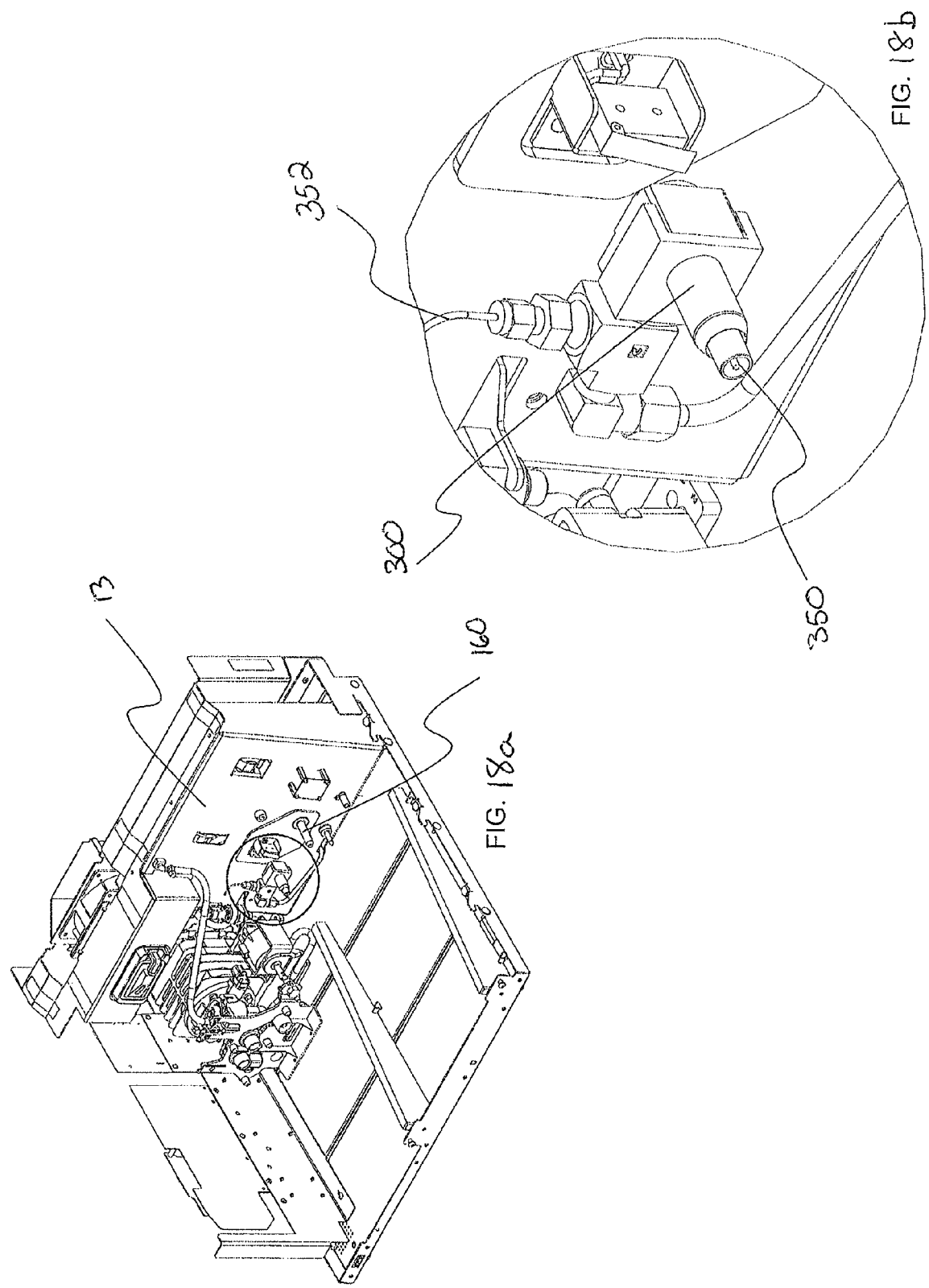

APPARATUS AND METHOD FOR DRYING INSTRUMENTS USING SUPERHEATED STEAM

CROSS REFERENCE TO RELATED APPLICATION

This application is a national stage of PCT/CA2007/001197, and claims the benefit under 35USC §120 of U.S. application Ser. No. 11/481,910, which was filed on July 7, 2006 and is now abandoned.

FIELD OF THE INVENTION

The present invention relates to apparatus for drying medical or dental instruments and the like using superheated steam.

BACKGROUND OF THE INVENTION

When steam is heated to a temperature above the boiling point corresponding to its pressure, it becomes superheated steam. Superheated steam has a greater heat capacity than air due to its water content and is therefore capable of delivering more heat energy to an instrument to be dried, thus vaporizing moisture more efficiently. This property of superheated steam has been exploited in a number of industries including the food and paper industries.

In known steam sterilization processes which are used to sterilize medical or dental instruments and the like, unless they are to be used immediately, the instruments must be dried after they have been sterilized. Air (hot or room temperature) is often used to perform this drying step. Heat energy from the air is transferred to the instruments to vaporize any residual moisture on the instruments or within the sterilization chamber. Residual moisture on the instruments is also evaporated by the release of the heat stored in the instruments, in which case the air acts as a carrier to remove the evaporated moisture. The use of air for drying is not particularly effective if the instruments are wrapped or pouched or if the instruments have a shape that traps moisture. In particular, sterilization pouches which are typically used in the medical and dental industries tend to retain water and air drying of these pouches can be both ineffective and time-consuming.

There are also known steam sterilization processes which involve vacuum-assisted drying where chamber pressure is lowered by means of drawing a vacuum to decrease the boiling point of the condensate causing it to evaporate more rapidly. This process requires a vacuum pump in addition to heating means which is costly and requires a leak-tight system to operate.

U.S. Pat. No. 6,026,588 discloses a superheated vapour dryer system for the precision removal of water from parts including disk drive media, flat panel displays and the like. The system boils and condenses solvents such as isopropyl alcohol to remove water and other contamination from the parts. After the parts have been treated with a liquid solvent, they are exposed to superheated vapours. As heat from the superheated vapours is transferred to the parts, any liquid solvent remaining will be boiled off. The parts are supported by a moving tray or suspended from hooks so that they may be immersed in and removed from a supply of liquid solvent. The parts are exposed to the superheated vapours by moving them through a so-called 'vapour zone'. This type of system is not well-suited to the medical/dental sterilization industry in terms of size and speed requirements.

A number of prior patents in the field of medical/dental sterilization disclose the use of superheated steam for sterilization. U.S. Pat. No. 1,902,625 (Dunham) discloses a steam sterilizer in which superheated steam is fed into a sterilization chamber via a plurality of expansion nozzles to sterilize instruments. U.S. Pat. No. 1,377,725 (Pentz) also discloses a steam sterilizer in which steam at a temperature 'high above the boiling point' is fed into a sterilization chamber via a plurality of openings in the walls of the sterilization chamber. As the superheated steam cools after sterilization is complete, it will condense on Instrument surfaces.

SUMMARY OF THE INVENTION

Embodiments of the present invention provide apparatus for drying medical or dental instruments and the like using superheated steam, a method for drying such instruments using superheated steam, and a system for sterilizing using saturated steam and drying such instruments using superheated steam. By distributing superheated steam within an instrument chamber, many different types of load, including both pouched/wrapped instruments and loose instruments, may be quickly and effectively dried. The time required for drying the instruments using superheated steam is shorter than the time required for drying the Instruments using air because superheated steam has a higher heat capacity than air and is therefore able to transfer a greater amount of heat to vaporize any residual moisture. In the case of a cassette sterilizer or autoclave, the drying time using superheated steam as opposed to conventional heated compressed air was found to be shortened by as much as 75%.

In accordance with an embodiment of the present invention, there is provided an apparatus for drying instruments using superheated steam. The apparatus comprises a chamber for receiving the instruments, a steam generation means, a distribution means and an exhaust means. The chamber has at least one inlet port. The steam generation means generates superheated steam. The distributions means is connected to the at least one inlet port for distributing superheated steam from the steam generation means, through the inlet port, within the chamber. The exhaust means is for purging vaporized moisture from the chamber.

In accordance with a further embodiment of the invention, there is provided an apparatus for drying medical or dental instruments using superheated steam in a steam sterilization system for the sterilization of the instruments using saturated steam. The apparatus for drying comprises a chamber for receiving the instruments, a steam generation means, a distribution means and an exhaust means. The chamber has at least one inlet port. The steam generation means generates superheated steam. The distributions means is connected to the at least one inlet port for distributing superheated steam from the steam generation means, through the inlet port, within the chamber. The exhaust means is for purging vaporized moisture from the chamber.

In accordance with yet a further embodiment of the present invention there is provided a method of drying medical or dental instruments using superheated steam in a steam sterilization system. The steam sterilization system has a chamber for receiving the instruments, at least one inlet port for connection to a steam generation means and an exhaust means for purging vaporized moisture from the chamber. The method comprises the steps of sterilizing the instruments using saturated steam generated by the steam generation means and drying the instruments using superheated steam generated by the steam generation means to vaporize moisture within the chamber and purging the vaporized moisture from the chamber using the exhaust means.

BRIEF DESCRIPTION OF THE DRAWINGS

These and other advantages of the invention will become apparent upon reading the following detailed description and upon referring to the drawings in which:

FIGS. 12a and 12b are perspective views of a further embodiment of the invention;

FIG. 16 is a side sectional view of a chamber incorporating the distribution means shown in FIG. 13;

FIG. 17 is a side sectional view, partially cut away, showing the embodiment of FIG. 13;

FIG. 18a is a perspective view of the cassette sterilizer with cover, cassette and armature removed showing the inlet and outlet probes and FIG. 18b is a perspective view of the detailed section of FIG. 18a, showing an embodiment of an exhaust probe in detail;

Figure 1:
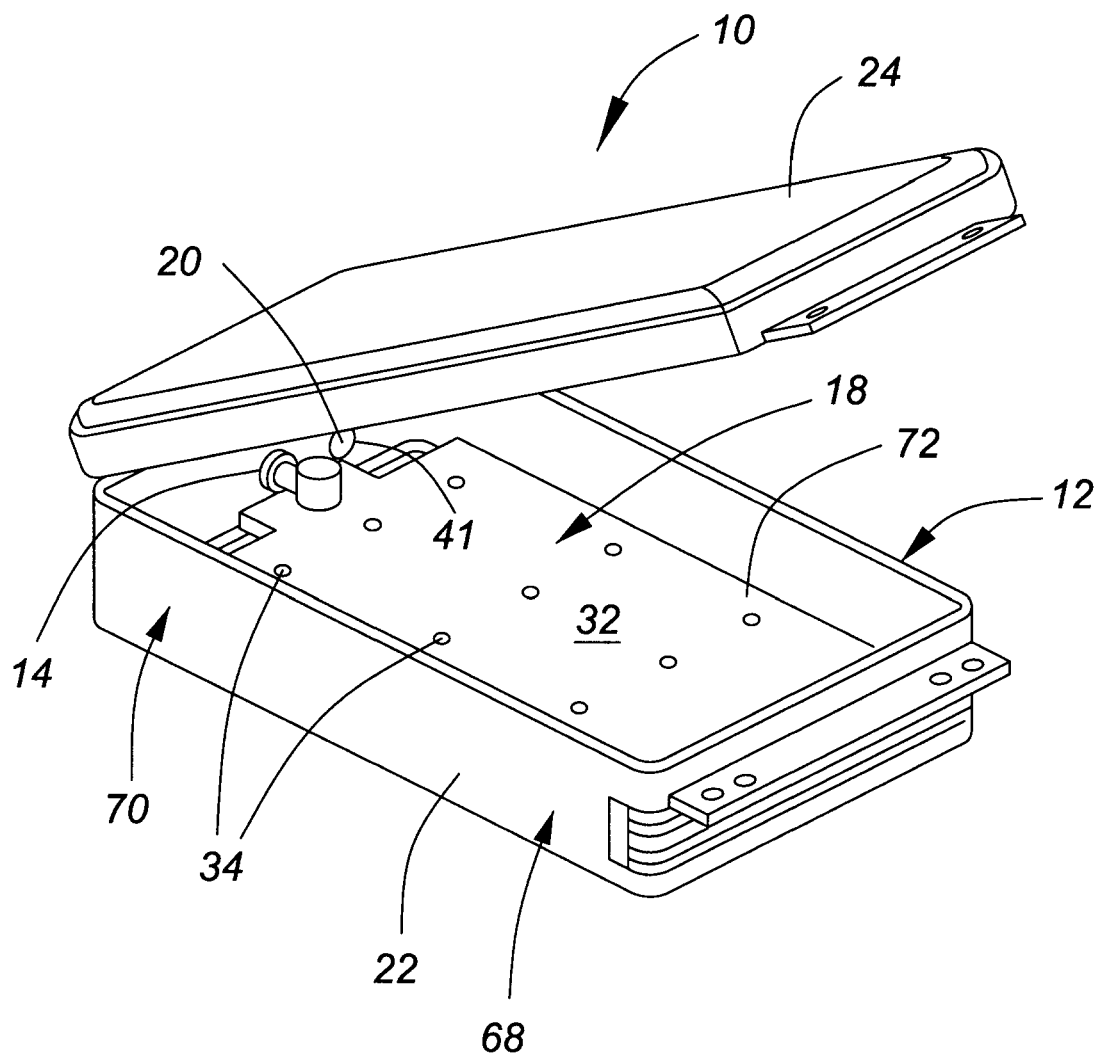
FIG. 1 is a perspective view of a chamber in accordance with an embodiment of the Invention.

While the invention will be described in conjunction with the illustrated embodiments, it will be understood that it is not intended to limit the invention to such embodiments. On the contrary, it is intended to cover all alternatives, modifications and equivalents as may be included within the spirit and scope of the invention as defined by the appended claims.

Detailed Description of the Preferred Embodiments

In the following description, similar features in the drawings have been given identical reference numerals where appropriate.

FIG. 1 illustrates an apparatus 10 for drying medical or dental instruments and the like using superheated steam. Apparatus 10 comprises a chamber 12 for receiving the instruments (not shown). Chamber 12 has an inlet port 14 (or more than one inlet port) for connecting the chamber 12 to a steam generation means 16 (not shown in FIG. 1) to transfer superheated steam from the steam generation means 16 to the chamber 12. Apparatus 10 further comprises a distribution means 18 connected to the inlet port 14 for distributing superheated steam within the chamber 12 and exhaust means 26 for purging vaporized moisture from the chamber 12. Exhaust means 26 may comprise an exhaust port 20, as illustrated in FIG. 1 (exhaust port 20 is shown in more detail in FIG. 11).

Figure 2:
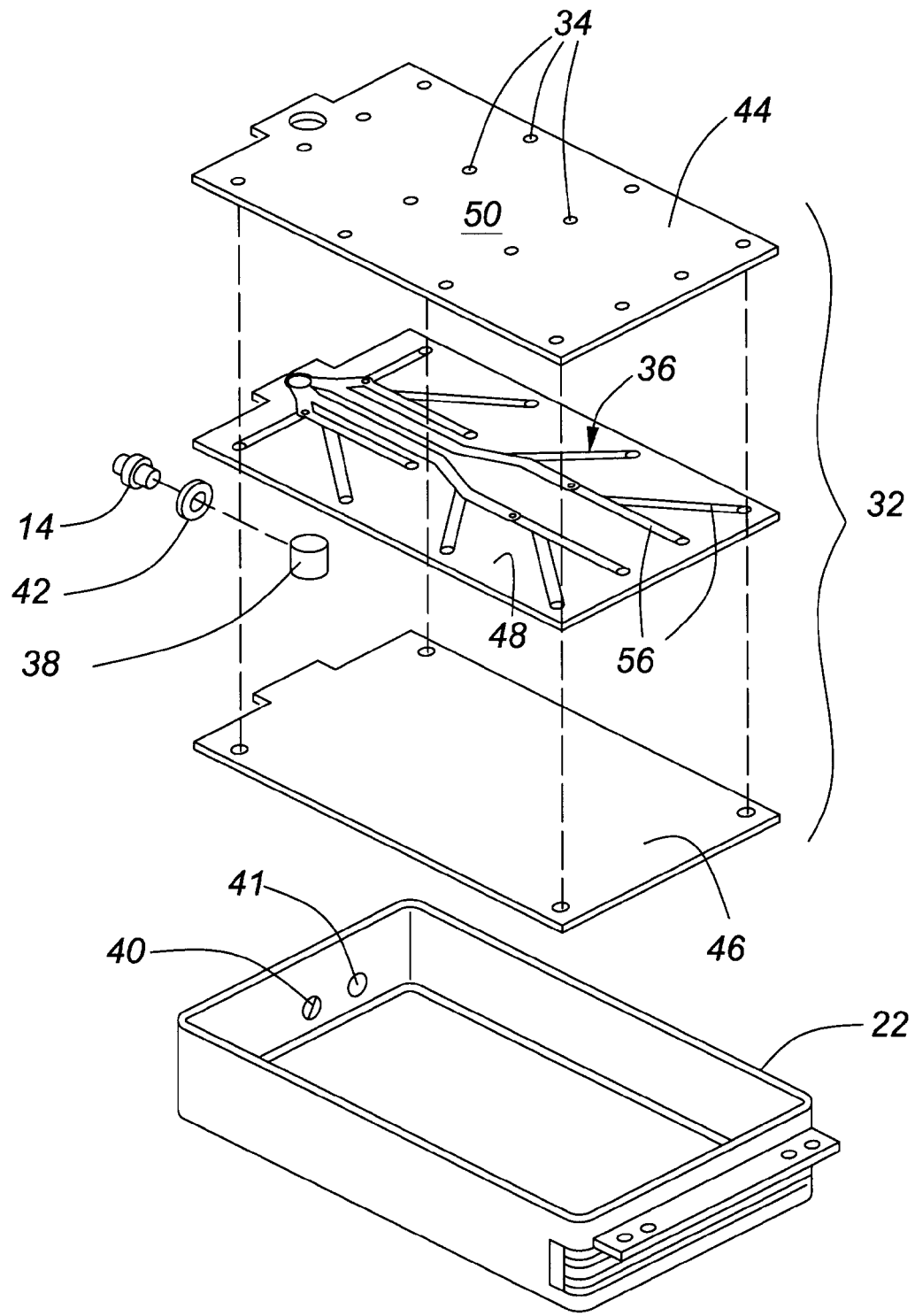
FIG. 2 is an exploded schematic top perspective view of a tray and manifold assembly of the chamber of FIG. 1.
Figure 3:
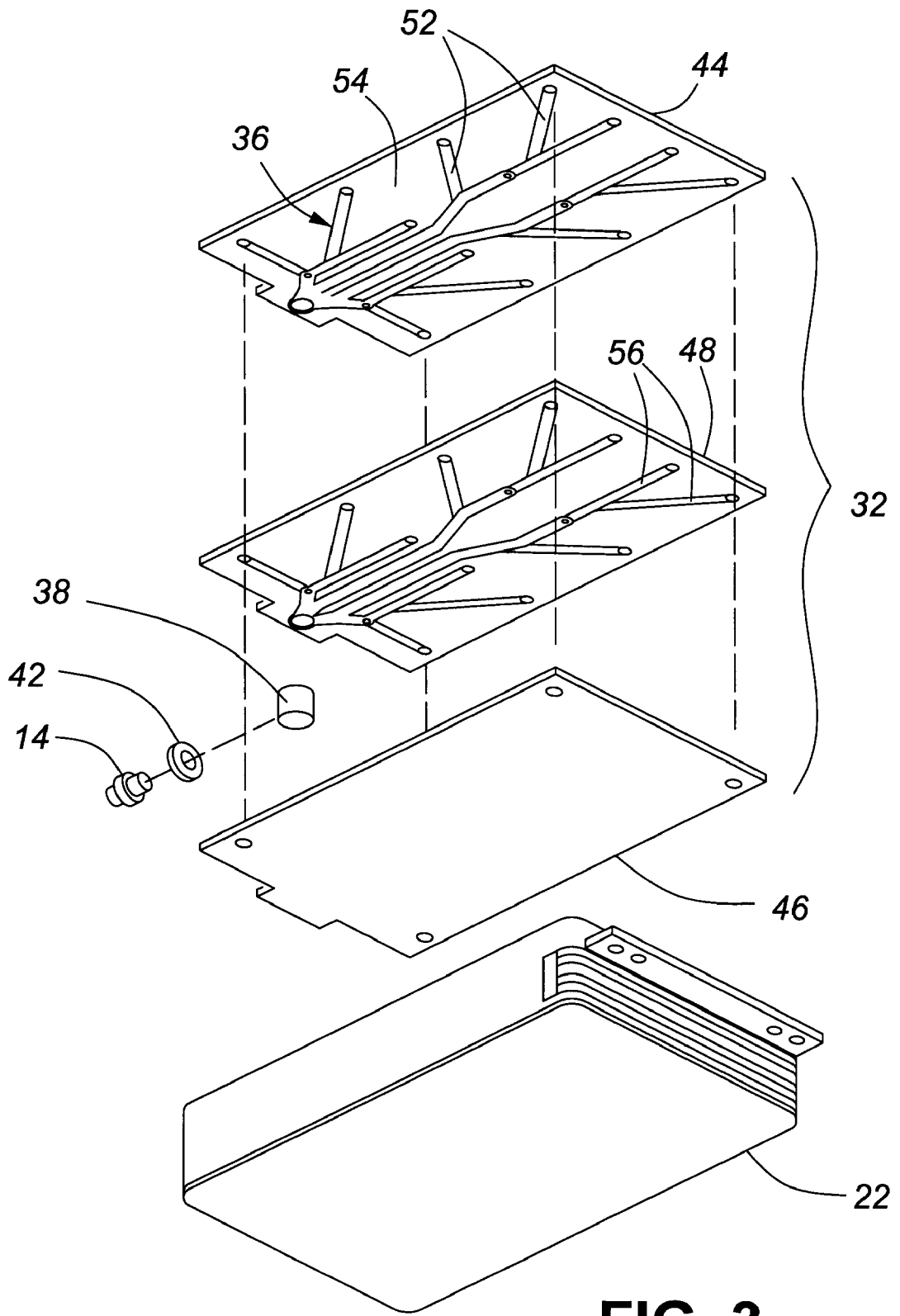
FIG. 3 is an exploded schematic bottom perspective view of the tray and manifold assembly of FIG. 2 and FIG. 1.

Chamber 12 may be a cassette, as illustrated in FIGS. 1 to 3, but it will be appreciated by those skilled in the art that other chamber configurations suitable for holding instruments may be used. Chamber 12 shown in FIG. 1 to 3 comprises a tray 22 and a lid 24 for covering and sealing the tray 22.

At the end of a sterilization process, the temperature of any residual moisture in the chamber 12 will drop and the moisture will have a tendency to condense on the instruments. By distributing superheated steam within the chamber 12, the moisture which has condensed on the instruments will be re-vaporized. The re-vaporized moisture may then be flushed out the exhaust port 20.

The instruments that are received by the chamber 12 may be instruments that have been sterilized using a steam sterilization process, instruments that have been washed using an instrument washer, instruments that have been disinfected using an instrument disinfector or any other damp instruments. Chamber 12 may also be used during a steam sterilization process, as will be described in more detail later in this description. Similarly, chamber 12 may be used during a washing process and/or during a disinfecting process.

Distribution means 18 may be any suitable means for distributing superheated steam within the chamber 12 such as a point source diffuser. Referring to FIGS. 2 and 3, distribution means 18 may be a manifold assembly 32 which comprises a plurality of distributed steam ports 34 connected by a plurality of interconnected conduits 36. Interconnected conduits 36 are connected to the inlet port 14 via a manifold port 38. As shown, inlet port 14 is coupled to the manifold port 38 through an opening 40 in the chamber 12. Exhaust port 20 is coupled to the chamber 12 though an opening 41 in the chamber 12. A nut 42 and/or any other suitable connector parts may be used to couple the inlet port 14 and the manifold port 38. Manifold assembly 32 may be located in a bottom portion of the tray 22 or any other suitable part of the chamber 12

It should be noted that by distributing superheated steam using the distribution means 18 within chamber 12, the drying time for a load of instruments can be significantly reduced. For example, in tests of a load in a cassette-type sterilizer, the drying time has been measured to be reduced by at least 33% compared to that without using distribution means 18. Those skilled in the art will recognize that the overall drying time will vary from these test results. Nevertheless, this represents a significant improvement over existing sterilizer drying systems. Without using distribution means 18 to distribute superheated steam within the chamber 12, it is very difficult to achieve complete dryness within the chamber 12 as the vaporized moisture will recondense as the chamber 12 cools due to heat loss to the surrounding. Additional heat cannot be applied to the chamber 12 through inlet port 14 to prevent re-condensation as the chamber 12 must be kept below a maximum allowable temperature that is dictated by the load, as will be discussed in more detail later in this description. Moreover, cassette-type sterilizers are not usually equipped with additional heaters around the cassette (such as a band heater) that could be used to prevent re-condensation before drying is complete.

Interconnected conduits 36 may be a plurality of interconnected tubes. These interconnected tubes may be made up of metal, silicone, Teflon™ or other suitable materials. Alternatively, interconnected conduits 36 may be a plurality of interconnected channels, as shown in FIGS. 2 and 3.

Manifold assembly 32 may comprise a top manifold plate 44, a bottom manifold plate 46 and a planar gasket 48 disposed between the top manifold plate 44 and the bottom manifold plate 46. Steam ports 34 are distributed on a top surface 50 of the top manifold plate 44 and are connected to a plurality of grooves 52 on a bottom surface 54 of the top manifold plate 44, as shown in FIG. 3. Planar gasket 48 also has a plurality of grooves 56 corresponding to the grooves 52 of the top manifold plate 44. Planar gasket 48 is positioned in sealing contact with the bottom surface 54 of top manifold plate 44 to form the interconnected conduits 36 by coupling together the grooves 52 on the bottom surface 54 of the top manifold plate 44 and the grooves 56 on the planar gasket 48. Interconnected conduits 36 are connected to manifold port 38.

The top manifold plate 44 and the bottom manifold plate 46 may be constructed of a high temperature thermoplastic. The planar gasket 48 may be made from silicone rubber. Those skilled in the art will appreciate and understand of course that other suitable materials may be used.

Alternatively, manifold assembly 32 may comprise a top manifold plate 44 and a bottom manifold plate 46 without a planar gasket 48. A plurality of grooves 52 may be provided in one or both of the top manifold plate 44 and the bottom manifold plate 46. The top manifold plate 44 and the bottom manifold plate 46 may be sealed together to form the interconnected conduits 36. Sealing may be accomplished by ultrasonic spot welding between contacting surfaces of the plates and/or placement of sealing material between contacting surfaces of the plates.

For a homogeneously damp load, the most efficient drying occurs when the entire load reaches a dry state simultaneously. Thus for an evenly distributed load, steam ports 34 are preferably evenly distributed within the chamber 12. It should of course be understood that chamber 12 may be configured for a specific load which is not necessarily evenly distributed within the chamber 12 by adapting the arrangement of steam ports 34 to the shape of the load.

In order to dry an entire randomly positioned load simultaneously, uniform thermal power must be delivered by the superheated steam across the chamber 12 for the duration of the drying process. Thermal power is a function of both temperature and mass flow rate of the superheated steam. The superheated steam will inevitably lose heat energy as it moves away from the inlet port 14 so that steam being delivered to the front portion 68 of the chamber 12 is cooler than steam being delivered to the rear portion 70 of the chamber 12. Heat energy will also be lost through the periphery 72 of the chamber 12. These effects can be compensated for by increasing the mass flow rate through the steam ports 34 which are located in the front portion 68 of the chamber 12 and the steam ports 34 which are located close to the periphery of chamber 12. The mass flow rate can be increased by increasing the size of the conduits 36 and/or increasing the diameter of the steam ports 34.

As heat energy is being transferred from the superheated steam to the instrument load and the chamber 12, the superheated steam itself will cool down and approach a saturated state. Once the steam temperature drops below the saturated steam curve at a given chamber pressure, steam will start to condense back to liquid water. This is highly undesirable as the condensate will re-wet the instrument load and the chamber 12. In order to avoid superheated steam from re-condensing, thermal power must be distributed in such a way so as to maintain a minimum chamber temperature that is above the saturated steam curve for a given chamber pressure. This can be achieved by biasing the locations of some of the steam ports 34 towards the interior space of the chamber 12 and distributing the remaining steam ports 34 towards the instrument load.

An optional temperature sensor, which is preferably located at the coldest spot inside the chamber, can be used to monitor the chamber temperature to ensure the minimum chamber temperature is attained throughout the entire drying phase of the cycle. The optional temperature sensor can also be used as a dryness indicator to indicate the end of the drying phase. As the condensate in the instrument load and the chamber 12 evaporate, less heat energy is required as there is no need to overcome any latent heat of vaporization of water. This will result in an increase in chamber temperature and which can be detected by the said temperature sensor. It is understood that this optional temperature sensor can also be a chamber temperature sensor used to monitor the steam temperature during the sterilization process.

A number of suitable conduit and steam port arrangements have been contemplated, which will now be described with reference to FIGS. 4 to 8. It should be understood that these arrangements are examples and that embodiments of the invention may comprise any suitable port and conduit arrangement.

Figure 4:
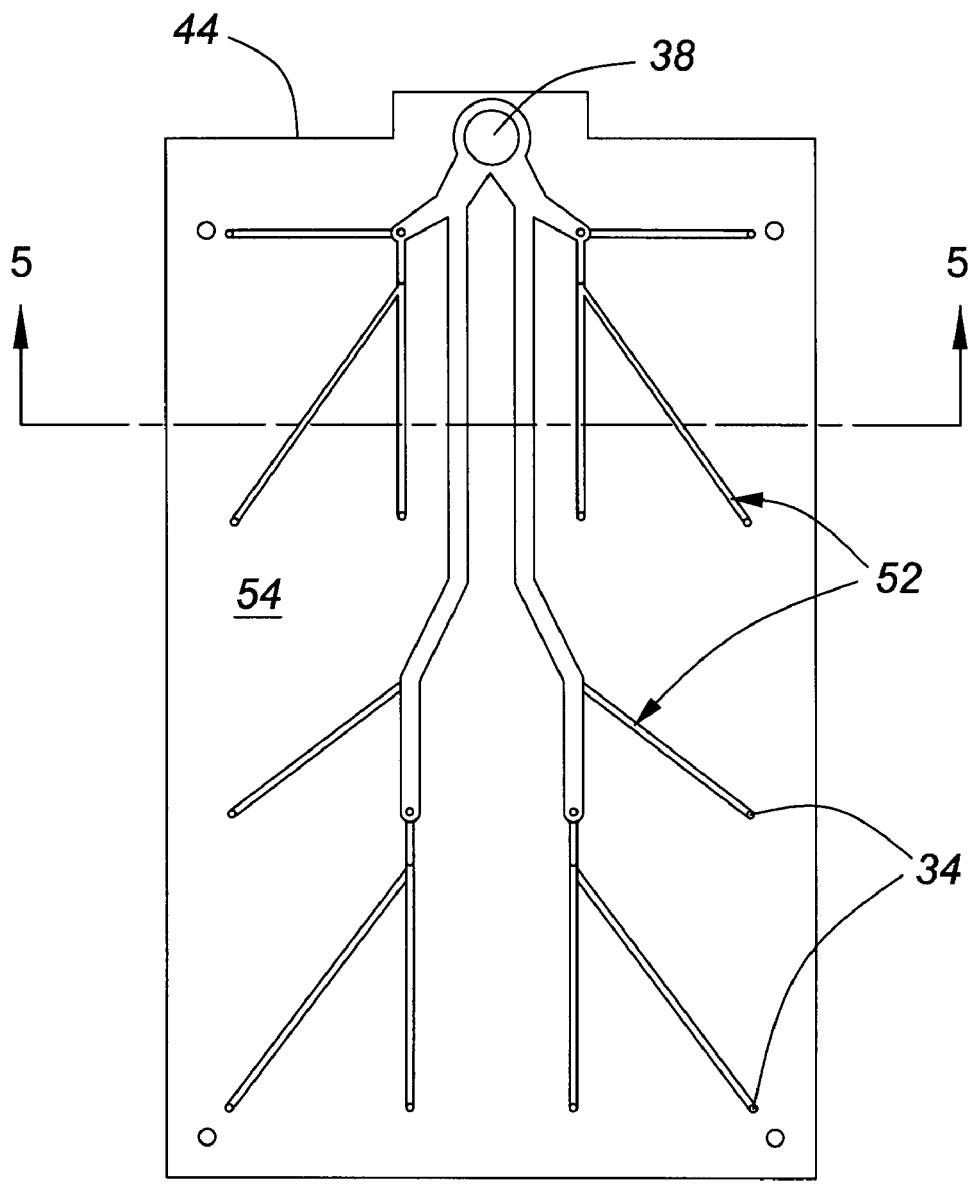
FIG. 4 is a bottom view of a top manifold plate of the manifold assembly of FIGS. 1 to 3.
Figure 5:
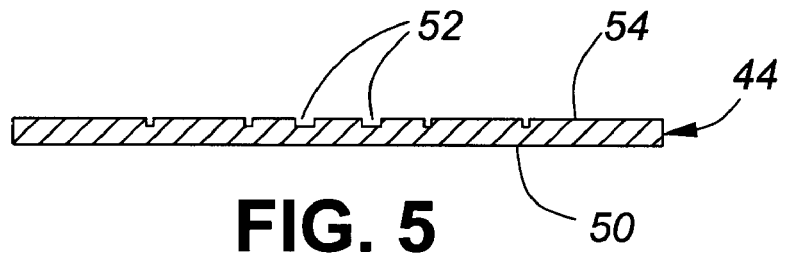
FIG. 5 is a section view of the top manifold plate of FIG. 4 along the line 5-5.

FIGS. 4 and 5 illustrate the top manifold plate 44 of the manifold assembly 32 shown in FIGS. 2 and 3. The sizes of grooves 52 are progressively smaller as they branch away from the superheated steam inlet in order to maintain a relatively constant mass flow rate throughout the entire manifold. The grooves 52 are arranged in a fractal branching arrangement similar to the fractal branching arrangement of bronchial tubes in a mammalian lung. These arrangements also attempt to minimize the sharpness of steam turns in order to minimize back pressure. Grooves 52 are connected to manifold port 38, as shown.

Figure 6:
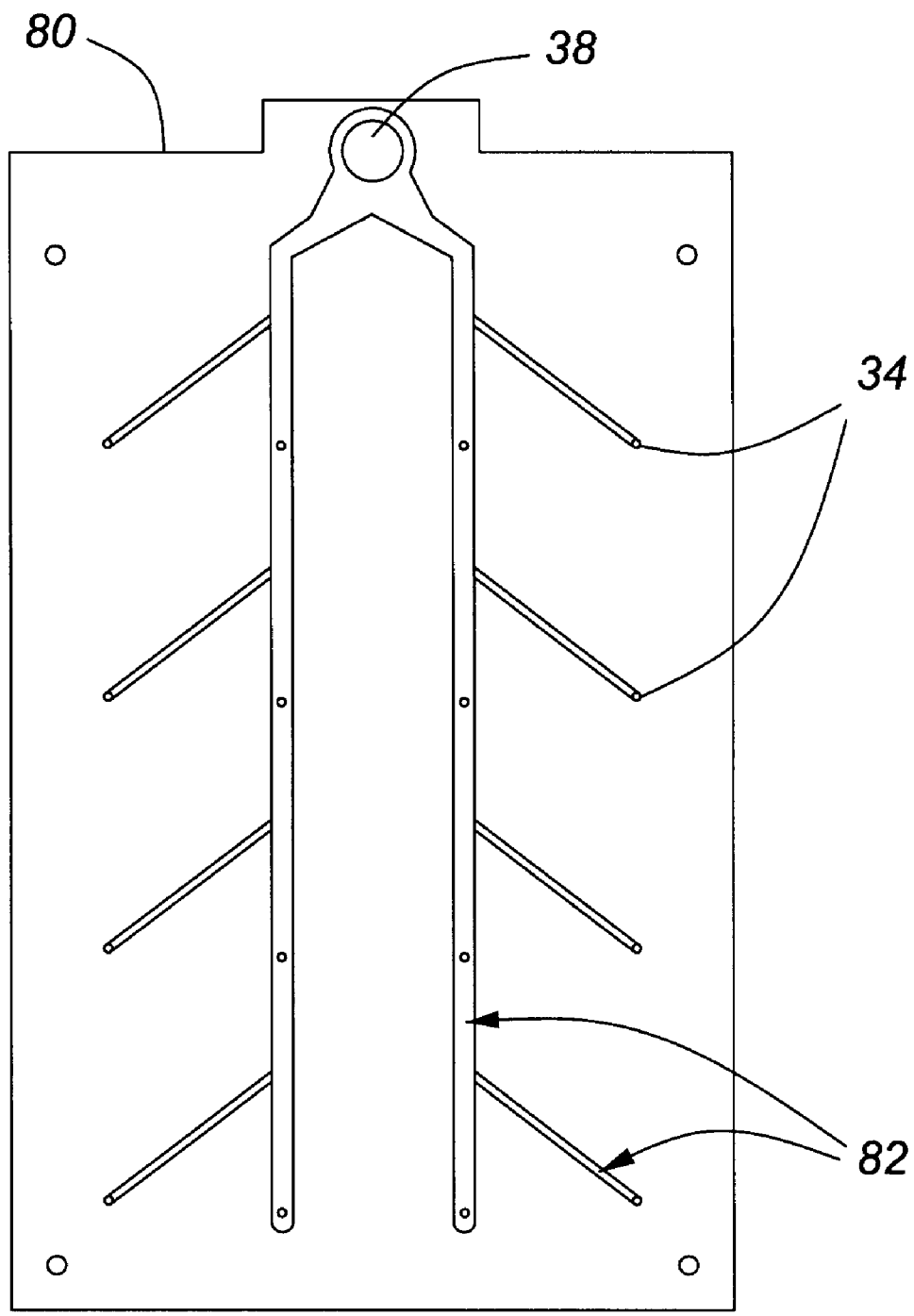
FIG. 6 is a bottom view of an alternative top manifold plate.

FIG. 6 illustrates an alternative top manifold plate 80 in which the grooves 82 are arranged in a fractal branching arrangement which is somewhat simpler that the arrangement shown in FIG. 4 for ease of fabrication. Grooves 82 are connected to manifold port 38, as shown.

Figure 7:
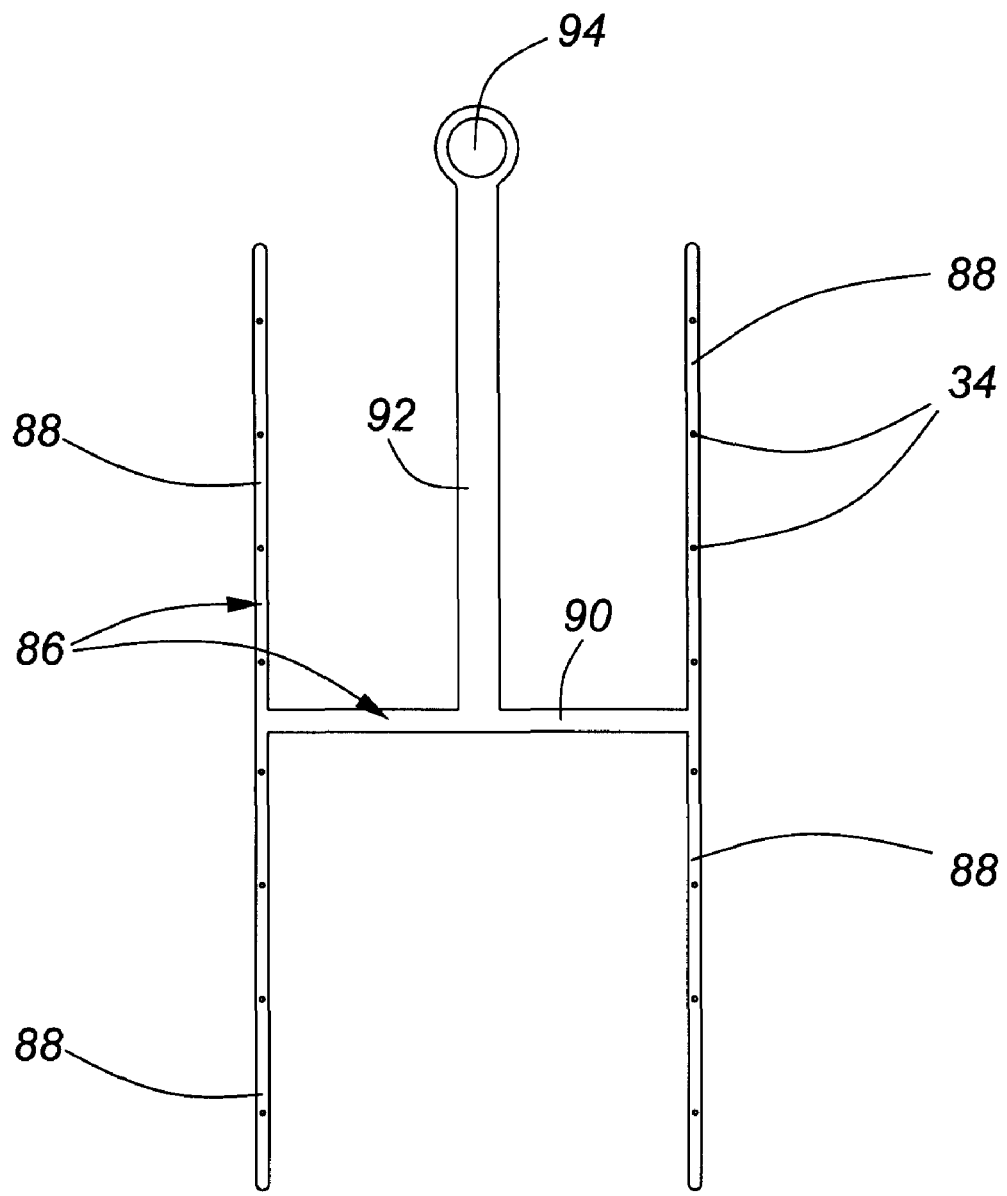
FIG. 7 is a bottom view of another alternative top manifold plate.

FIG. 7 illustrates another alternative configuration of conduits 36 in which tubes 86 are arranged in an H-shape having four leg portions 88, a bridge portion 90 and an inlet portion 92. Steam ports 34 may be distributed along the four leg portions 88. Inlet port 14 of the chamber 12 may be connected to the bridge portion 90 via the inlet portion 92 which is connected to port 94. This arrangement is designed to provide a symmetric steam distribution as each leg 88 is of the same length. Steam ports 34 can be designed such that the steam ports 34 furthest from the inlet have a larger diameter than the steam ports 34 closer to the inlet so as to allow more flow to the furthest steam ports 34 to compensate for the decrease in superheated steam temperature at those locations and hence maintain an even thermal power delivery throughout the chamber 12.

Figure 8:
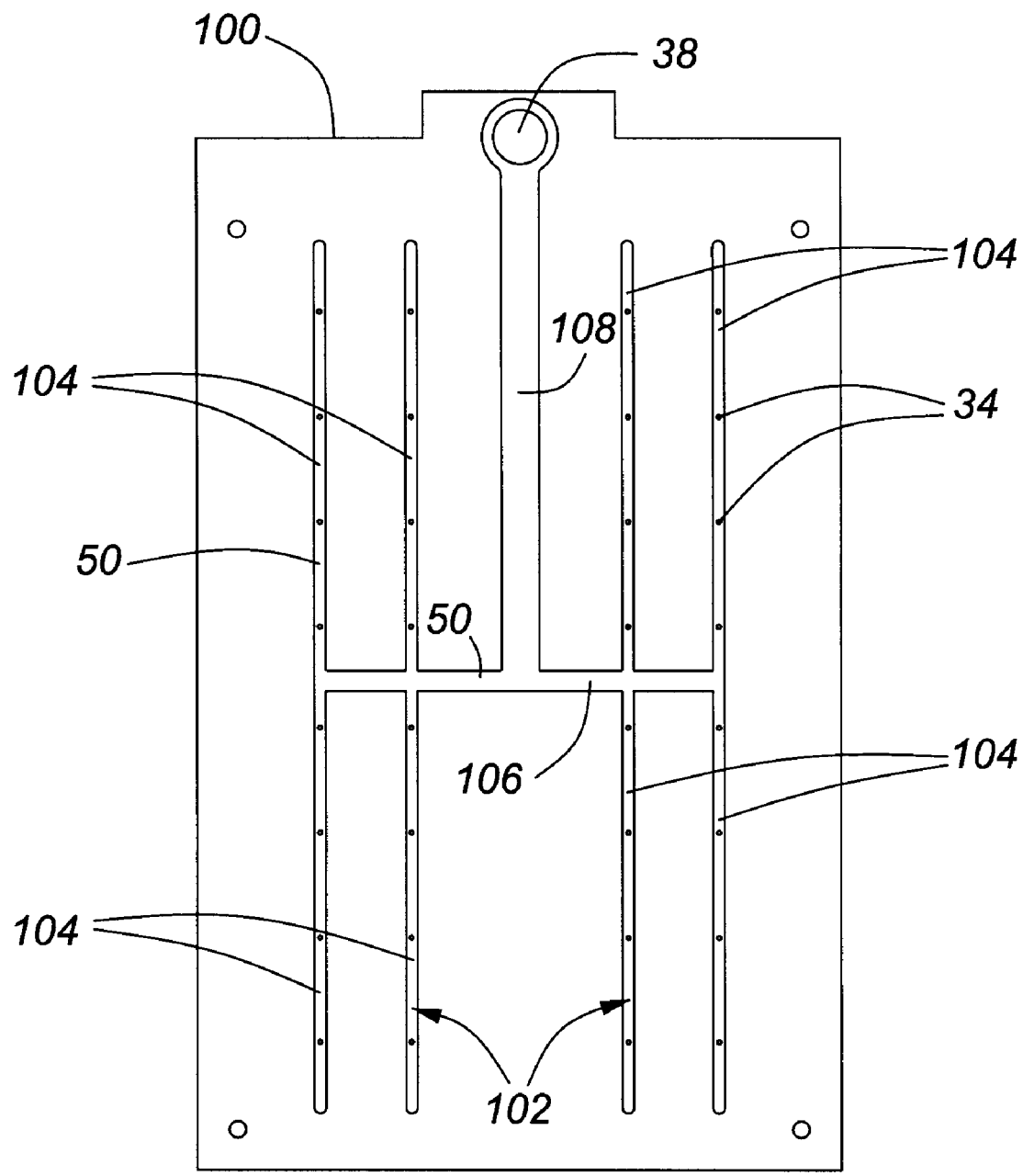
FIG. 8 is a bottom view of yet another alternative top manifold plate.

FIG. 8 illustrates yet another alternative top manifold plate 100 in which grooves 102 are arranged in a double H-shape having eight leg portions 104, a bridge portion 106 and an inlet portion 108. Steam ports 34 may be distributed along the eight leg portions 104. Inlet port 14 of the chamber 12 may be connected to the bridge portion 106 via the inlet portion 108 which is connected to manifold port 38. This arrangement is designed to provide better coverage across the chamber 12. As before, the diameter of the steam ports 34 can be adjusted to balance superheated steam flow and temperature in order to obtain an even thermal power distribution anywhere in the chamber 12. It should be noted that further multiple H-shape configurations of conduits 36 have been contemplated.

Figure 9:
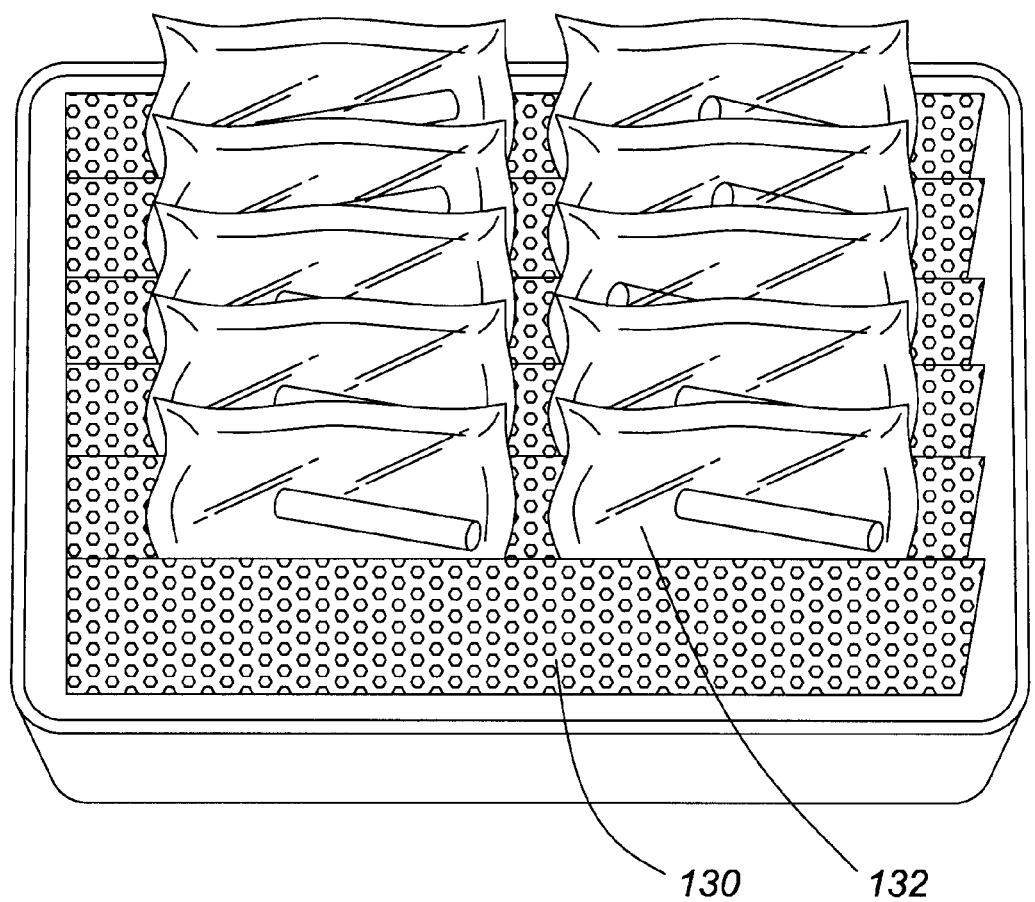
FIG. 9 is a perspective view of a drying rack.

Referring now to FIG. 9, chamber 12 may be configured to receive a perforated drying rack 130 for supporting and arranging the instruments within the chamber 12. For example, pouches 132 containing instruments may be arranged evenly within the chamber 12 by placing them in the perforated drying rack 130. The perforated drying rack 130 is preferably made of metal such as aluminum which stores heat energy quickly during the sterilization process and releases heat quickly to the surrounding instruments after sterilization. The perforations in the perforated drying rack 130 allow superheated steam from the manifold to pass through the perforated drying rack 130 in order to reach the load during drying. The advantage of the perforated drying rack 130 illustrated in FIG. 9 is that it provides support for pouched loads while allowing superheated steam to rise through the perforations and dry the load more effectively than a solid rack would. Moreover, its lower thermal mass translates into a more rapid sterilization cycle. The perforated drying rack 130 is nonetheless merely an example and it should be understood that chamber 12 could be configured to receive any suitable drying rack. Furthermore, it should be considered that the superheated steam distribution conduit or plate configuration could be integrated into the perforated drying rack so as to combine their respective functions into a single part. This will be discussed in greater detail with reference to the embodiment of the invention shown in FIGS. 12 to 17.

Apparatus 10 may be used independently or integrated into a steam sterilization system for sterilizing medical or dental instruments and the like using saturated steam, such as that disclosed in Applicant's co-pending PCT application No. WO 00/59553, the contents of which are incorporated herein by reference. Similarly, apparatus 10 may be integrated into washer systems and washer/disinfector systems such as those used in the medical and dental industries, as would be understood by the person skilled in the art. For example, in a washer system, the washing chamber could be chamber 12.

Figure 10:
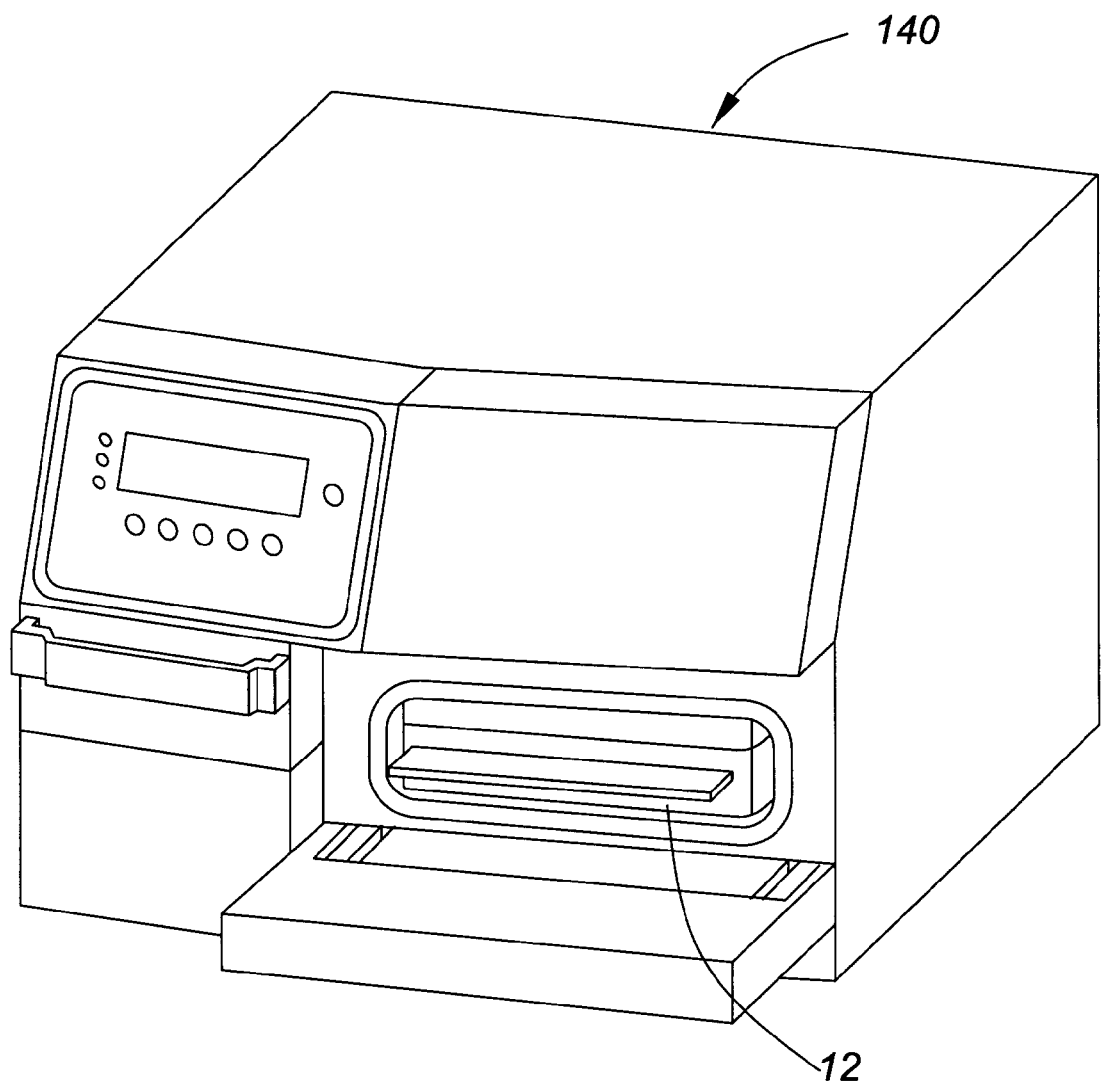
FIG. 10 perspective view of a steam sterilization and superheated steam drying system in accordance with an embodiment of the invention.
Figure 11:
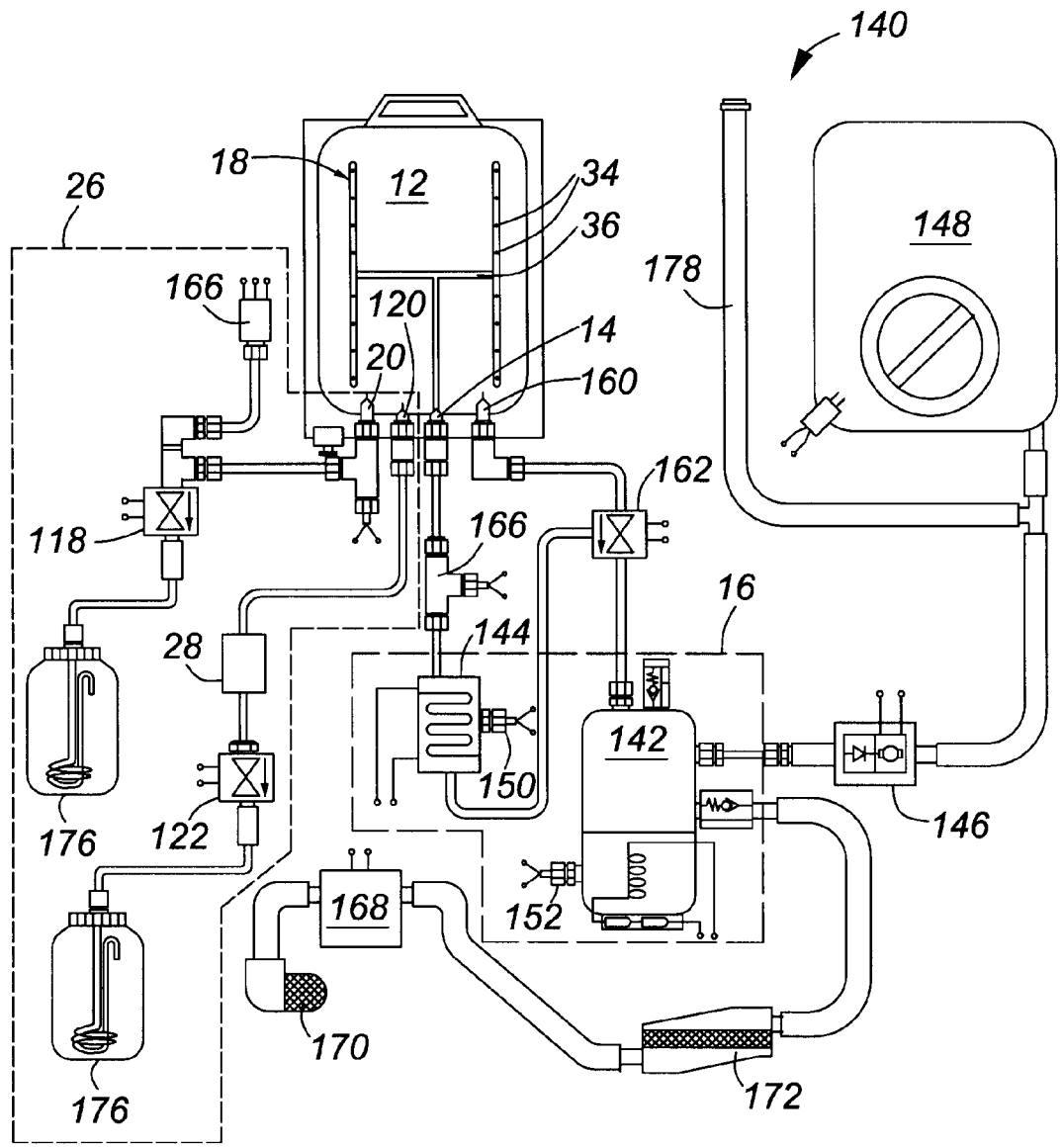
FIG. 11 is a block diagram of the system of FIG. 10.

FIG. 10 illustrates a steam sterilization and superheated steam drying system 140. FIG. 11 is a block diagram of the steam sterilization and superheated steam drying system 140 of FIG. 10. The steam sterilization and superheated steam drying system 140 will first sterilize the instruments using saturated steam and will subsequently dry the instruments using superheated steam. The steam sterilization and superheated steam drying system 140 may also perform other processes such as a conditioning process, a pressurizing process, and an air removal process, as would be understood by the person skilled in the art.

Steam generation means 16 may comprise a steam generator 142 and a superheated steam heater 144. Steam generator 142 generates saturated steam suitable for sterilization and may be a boiler, such as the boiler described in Applicant's co-pending Canadian application No. 2,481,635, the contents of which are incorporated herein by reference. Water is supplied from a water reservoir 148 and is injected into the steam generator by a water pump 146. A drain pip 178 may also be provided in order to drain water from the system 140, when required.

Superheated steam heater 144 may be any suitable heater such as a tubular or cartridge heater. It should be understood that the operating temperature of the superheated steam heater will depend upon drying requirements and temperature limitations of the load. Superheated steam heater 144 may be connected to a temperature sensor 150, for example a thermocouple, which can be used as a control input. Superheated steam heater 144 may also be connected to a temperature sensor 152, such as a thermocouple, which can be used as another control input.

During the sterilization process, saturated steam is generated by the steam generator 142 and directed via a first inlet port 160 into the chamber 12. During the drying process, superheated steam is generated by the superheated steam heater 144 by further heating of the saturated steam generated by the steam generator 142 and then injected via a second inlet port 14 (described previously) into the distribution means 18 in the chamber 12. A directional valve 162 may be provided to selectively direct steam from the steam generator 142 to the first inlet port 160 or steam from the steam generator 142 to the second inlet port 14 via the superheated steam heater 144. The directional valve 162 may be a three-way valve.

Alternatively, the steam generation means 16 may comprise a steam generator without a separate superheated steam generator. Such a steam generator would selectively produce saturated steam for sterilization of the instruments and superheated steam for drying of the instruments by selectively metering a received amount of water from a reservoir. The amount of water to be metered depends upon the watt density of the steam generator. It should be understood of course that any suitable steam generation means may be used.

While the term 'superheated steam' encompasses steam having any temperature above the boiling point of water, in the illustrated embodiments of the invention the superheated steam will reach the steam ports 34 at a temperature which does not exceed a maximum allowable temperature of the instruments as specified by the manufacturer. Exceeding the maximum allowable temperature of a particular material may cause thermal damage. Careful control of the superheated steam temperature may be achieved by, for example, keeping the pressure in the chamber 12 close to atmospheric pressure so that the temperature does not rise above the maximum sterilization temperature.

The most efficient superheated steam conditions occur when the pressure in the chamber is as low as possible so as to reduce the boiling point of water. For example, by keeping the pressure in the chamber 12 close as close to atmospheric pressure as possible, the energy required to evaporate moisture within the chamber 12 is reduced. The end result is a more efficient use of superheated steam and faster drying or equally fast drying but at a lower temperature, which is safer for the load. The apparatus 10 may be operable to provide a vacuum condition in the chamber 12, thus resulting in a lower water boiling point and therefore faster superheated steam drying for same steam temperature.

As shown in FIG. 11, exhaust means 26 may further comprises a normally-closed exhaust valve 118 which is connected to exhaust port 20 and is opened when vaporized moisture is to be purged from the chamber 12. More than one exhaust port and more than one corresponding exhaust valve may be provided. For example, as illustrated in FIG. 11, two exhaust ports 20 and 120 and corresponding exhaust valves 118 and 122 may be provided in order to purge at lower and higher exhaust rates by selectively opening one or both of the exhaust valves 118 and 122. The exhaust port(s) (20,120) may be opened when the exhaust valve(s) (118,122) is opened.

Alternatively, the exhaust port(s) (20,120) may be opened as the chamber 12 is inserted into a sterilization system. Similarly, the inlet port(s) may be opened as the chamber 12 is inserted into a sterilization system.

Exhaust means 26 may further comprise at least one moisture removal means 28. Moisture removal means 28 may be a vacuum pump or a heat exchanger operable to lower the pressure in the chamber 12 and draw evaporated moisture from the cassette. As explained previously, lowering the pressure in the chamber 12 reduces the boiling point of water for vaporization of moisture within the cassette. Of course, it should be understood that moisture removal means 26 is not limited to vacuum pumps and heat exchangers and is intended to encompass any suitable means for removing moisture from the chamber 12, as would be understood by those skilled in the art. Similarly, where moisture removal means 28 is positioned between exhaust port 120 and exhaust valve 122, it should be understood that moisture removal means 28 could be positioned between exhaust port 20 and exhaust valve 118 or in any other suitable position within system 140. Also, more than one moisture removal means 28 could be implemented. Vaporized moisture that has been purged from chamber 12 cools and may be collected in condensers 176.

Various additional temperature and pressure sensors 166 may be provided in the steam sterilization system in order to monitor and control the steam generation means 16, exhaust valve(s) (118,122) and directional valve 162. Sensors 166 are necessary where the steam sterilization system is to be compliant with industry standards. The configuration of these sensors 166 may be adapted to suit industry standards in different areas of the world. For example, the standards in Europe may differ from those in North America. It is conceivable that the same sensors required by sterilization standards could be used to control the superheated steam drying process.

It should be noted that apparatus 10 is scalable and could be adapted for both compact cassette-type steam sterilization systems and larger steam sterilization systems, such as large medical autoclaves and tunnel washers.

A method of drying medical or dental instruments using superheated steam in a steam sterilization system 140 will now be described. First, the instruments may be sterilized using saturated steam generated by the steam generation means 16. Next, the instruments may be dried using superheated steam generated by the steam generation means 16 to vaporize moisture within the chamber 12. During and/or after the drying step, the vaporized moisture is purged from the chamber 12 using the exhaust means 26.

Pulsing of superheated steam and or hot compressed air during superheated steam drying further improves the efficacy of the method. For pouched or wrapped loads, once the liquid moisture on the instruments in the pouches has been evaporated, the steam inside the wraps or pouches must then be purged before the temperature of the load drops at the end of the cycle or it will re-condense and soak the load and the paper or wrap. However, the paper or wrap is of low permeability, and flow between the inside of the pouch or wrap and the interior of the cassette is minimal. In an effort to increase the exchange of gasses between the interior of the pouch or wrap and the cassette, the exhaust valve can be alternatively closed and opened, creating a fluctuating pressure in the cassette. This has the effect of repeatedly collapsing and re-inflating the pouches, and encouraging a migration of gasses though the paper or wrap in the process. However, increasing the pressure in the cassette also decreases the available enthalpy of the superheated steam, reducing its moisture carrying capacity.

During and/or after drying of the instruments is complete, the chamber 12 may be flushed with air by injecting air through inlet port 160 into the chamber 12 in order to purge any residual moisture from the chamber 12 via the exhaust port(s) (20,120). This air flushing may last a few minutes, depending on the size and nature of the load, among other factors. The chamber 12 may also be flushed by, for example, introducing short-duration air pulses to evacuate vaporized moisture as it is formed.

It should be noted that where air flushing is performed, the moisture removal means may not be necessary. Of course, moisture removal using air flushing and moisture removal using the moisture removal means 28 discussed previously may each be used independently or in combination.

It should be noted that this air flushing step is particularly important where the pressure in the chamber 12 is kept close to atmospheric pressure, as described previously, because there may not be enough pressure to effectively force vaporized moisture out of the chamber 12 when the exhaust port(s) (20,120) and valve(s) (118,122) are opened, resulting in some re-condensation in the chamber 12 and on the load when the chamber is opened or allowed to cool down at the end of the drying cycle. Hot air may be used for flushing in order to prevent cooling of the chamber 12, but ambient air may also be used provided the superheated steam and chamber temperatures are sufficiently above the condensation point.

Air for the air flushing step may be supplied from a compressor 168 which may supply air through the steam generator 142 (as shown) or via a separate conduit to be injected into chamber 12. The ambient air supplied to the compressor 168 may be filtered by pre-filter 170. Similarly, air supplied from the compressor may be filtered by filter 172 which may be a microorganism retentive filter to avoid recontamination of the load during the air flushing step. The air flushing step may also be achieved using a heat exchanger or a vacuum pump to create suction force by rapid steam condensation to forcibly remove residual steam.

During sterilization, exhaust port 20 (the first exhaust port) and corresponding exhaust valve 118 may be opened during the sterilization step. A second exhaust port 120 and corresponding exhaust valve 122 may be opened during the drying and air flushing steps.

The exhaust valve 118 connected to the first exhaust port 20 may have a smaller orifice than the exhaust valve 122 connected to the second exhaust port 120 in order to precisely control the pressure in the chamber 12 during sterilization. The exhaust valve 122 connected to the second exhaust port 120 may have a larger orifice to ensure good flow of air and vaporized moisture from the chamber 12 and the lowest possible pressure in the chamber 12 during drying and air flushing. Of course, it is also contemplated that a single exhaust valve may be used to satisfy the exhaust requirements of sterilization, drying and air flushing.

Superheated steam drying in a cassette autoclave relies on effective in-flow of superheated steam to bring heat energy to the instrument load inside the cassette chamber. In order to prevent back pressure build up inside the cassette chamber, the exhaust of steam from the cassette chamber needs to be equally effective. In order to minimize back pressure build-up in the system, the dedicated exhaust valve 122 and a larger-diameter exhaust port 120 are used to maximize the mass flow of exhaust steam out of the system. The exhaust duct that is removably connected to the exhaust port must also have an unobstructed opening that corresponds to the exhaust port diameter in order to maintain the mass flow rate of the system.

However, adding a large opening in the exhaust duct may create a leak in the exhaust duct which in turn causes the exhaust duct to lose suction and fail to remove the condensate from the bottom of the tray, To address this issue, the use of two exhaust valves is contemplated, one that connects to a smaller diameter exhaust port for precise pressure control and another that connects to a larger diameter exhaust port for superheated steam drying. This single inlet, dual exhaust setup means three ports in the cassette which creates more potential leakage points as well as more seals and gaskets to maintain and replace There is thus illustrated in FIGS. 18 to 23 an embodiment of a concentric exhaust probe 300 with two separate connections to two separate exhaust valves suitable for use in this apparatus. The exhaust probe 300 is mounted on the cassette chassis 13 proximate to the inlet probe 160. As seen in FIG. 18b, the exhaust probe 300 houses the chamber thermocouple 350 and is in communication with the validation thermocouple 352.

Figure 19:
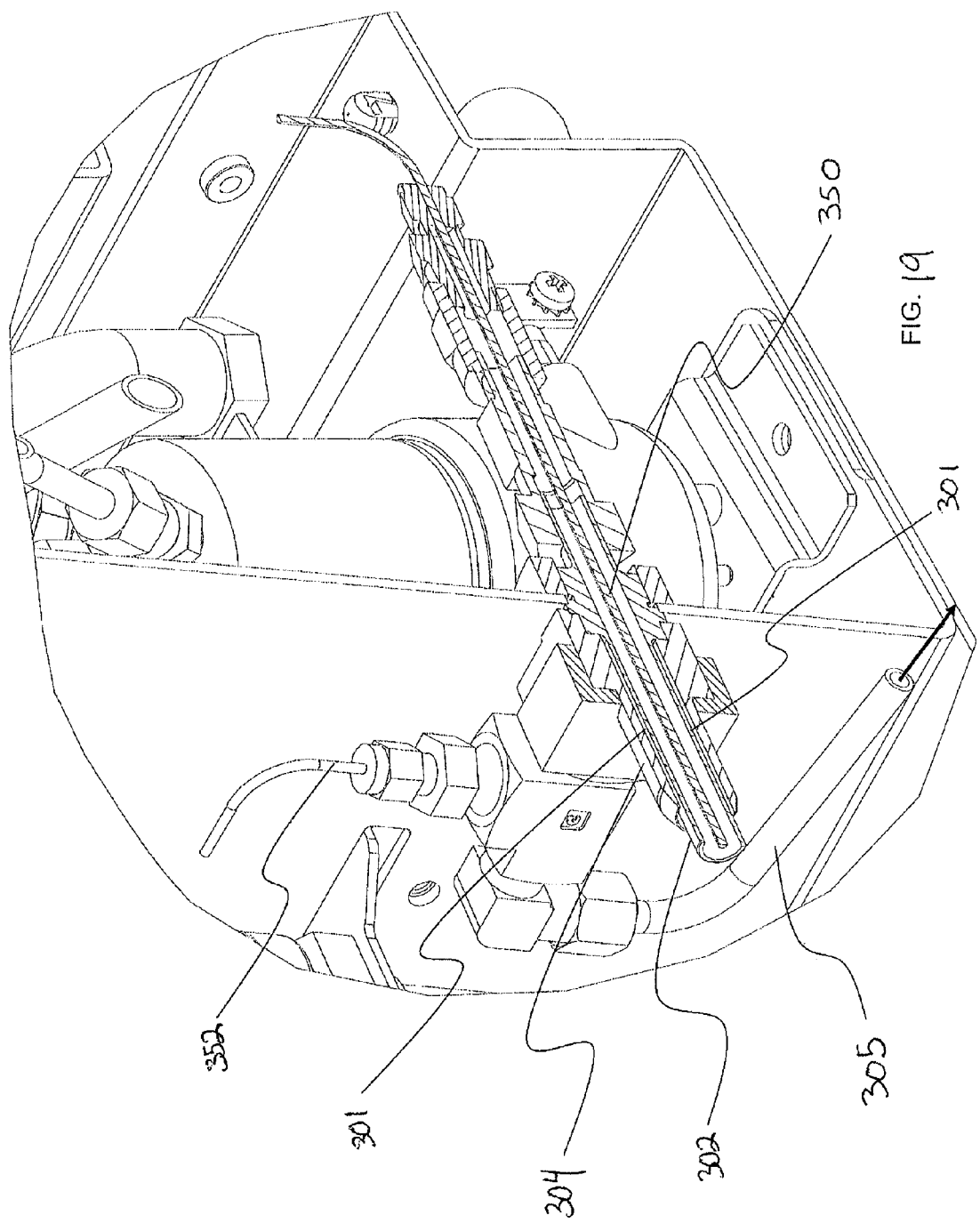
FIG. 19 is sectional view of the exhaust probe assembly of FIG. 18b.
Figure 20:
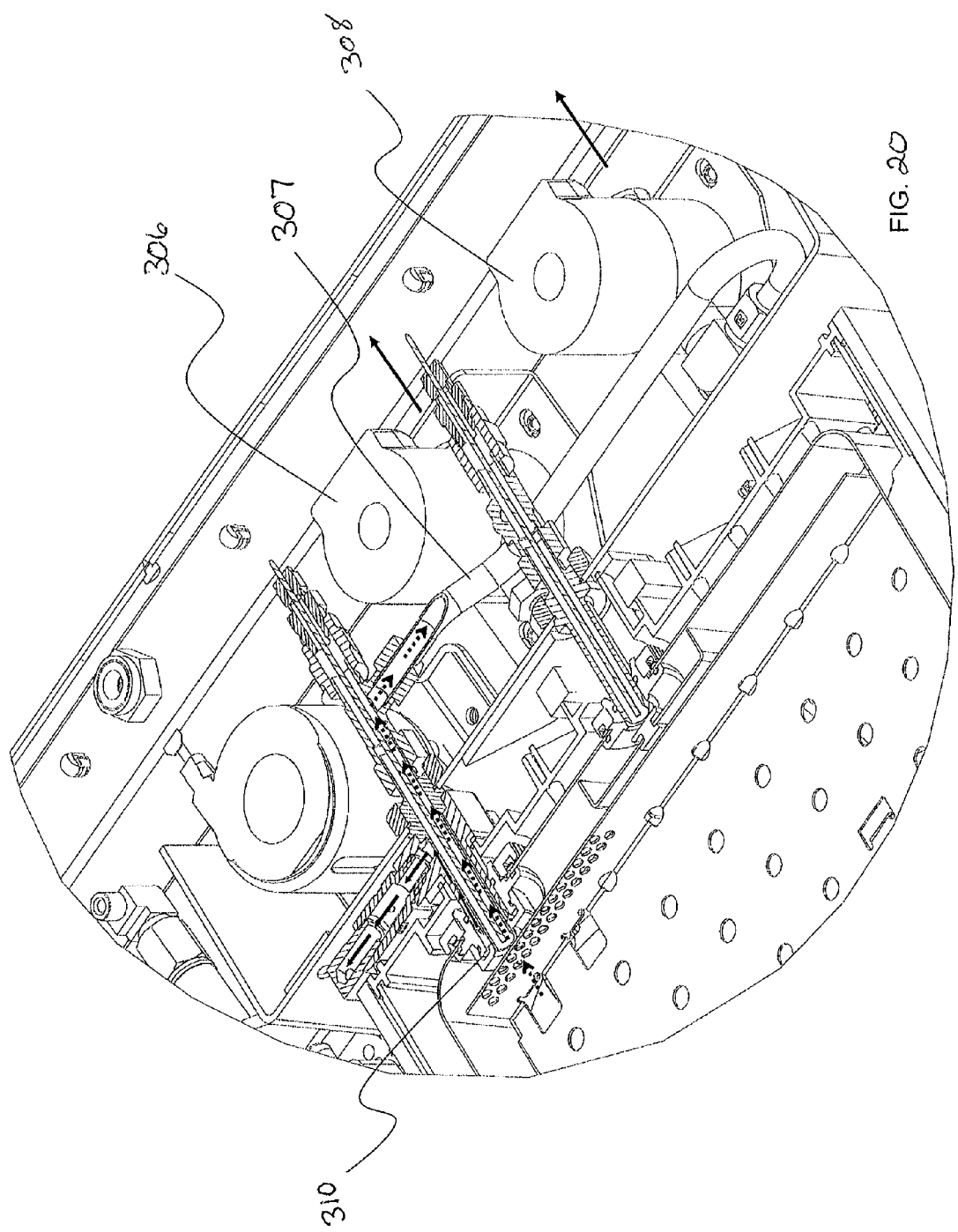
FIG. 20 is a sectional view of the inlet and exhaust probe assemblies.
Figure 21:
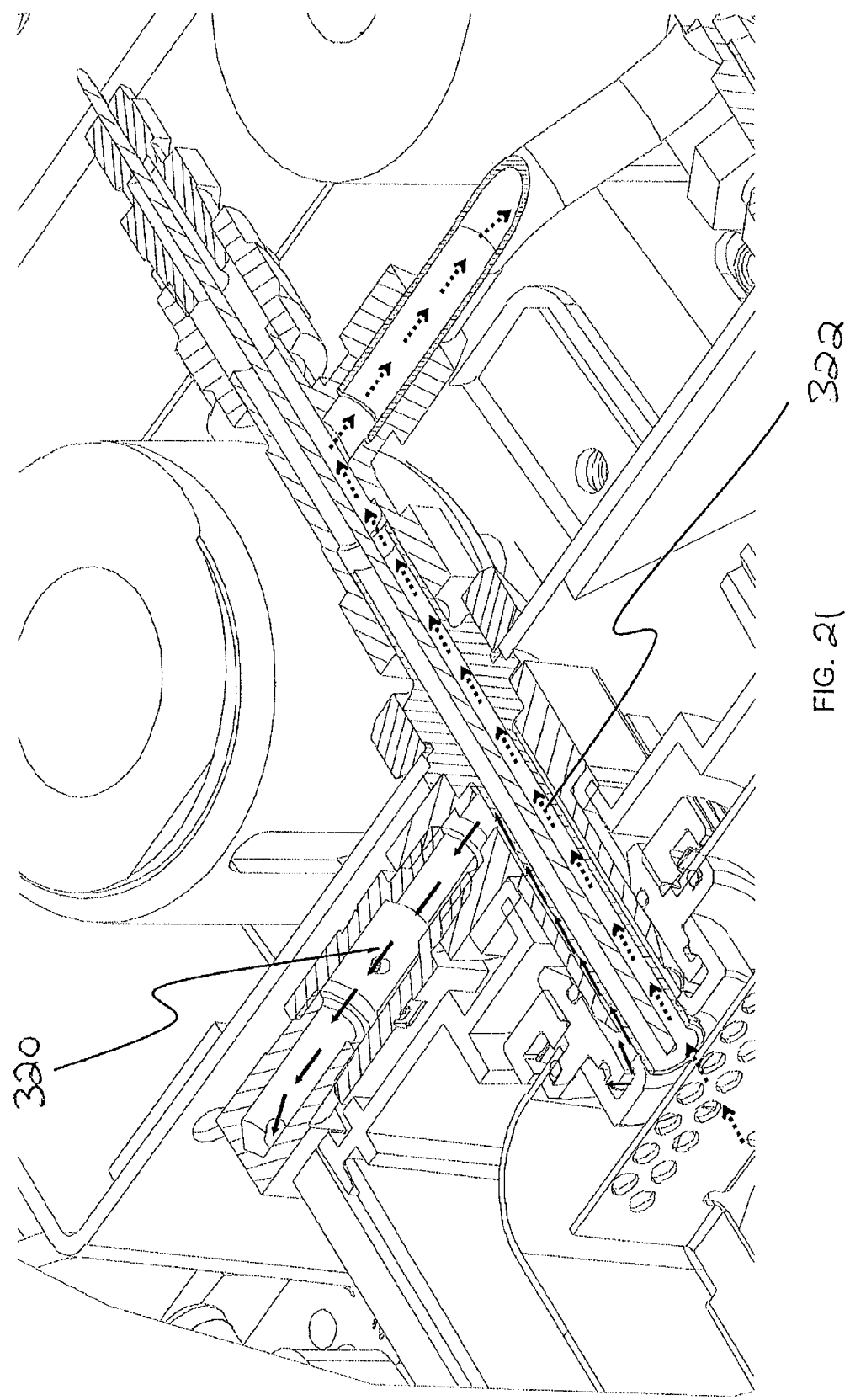
FIG. 21 is a sectional view of the exhaust probe assembly showing condensate path and superheated steam path.
Figure 22:
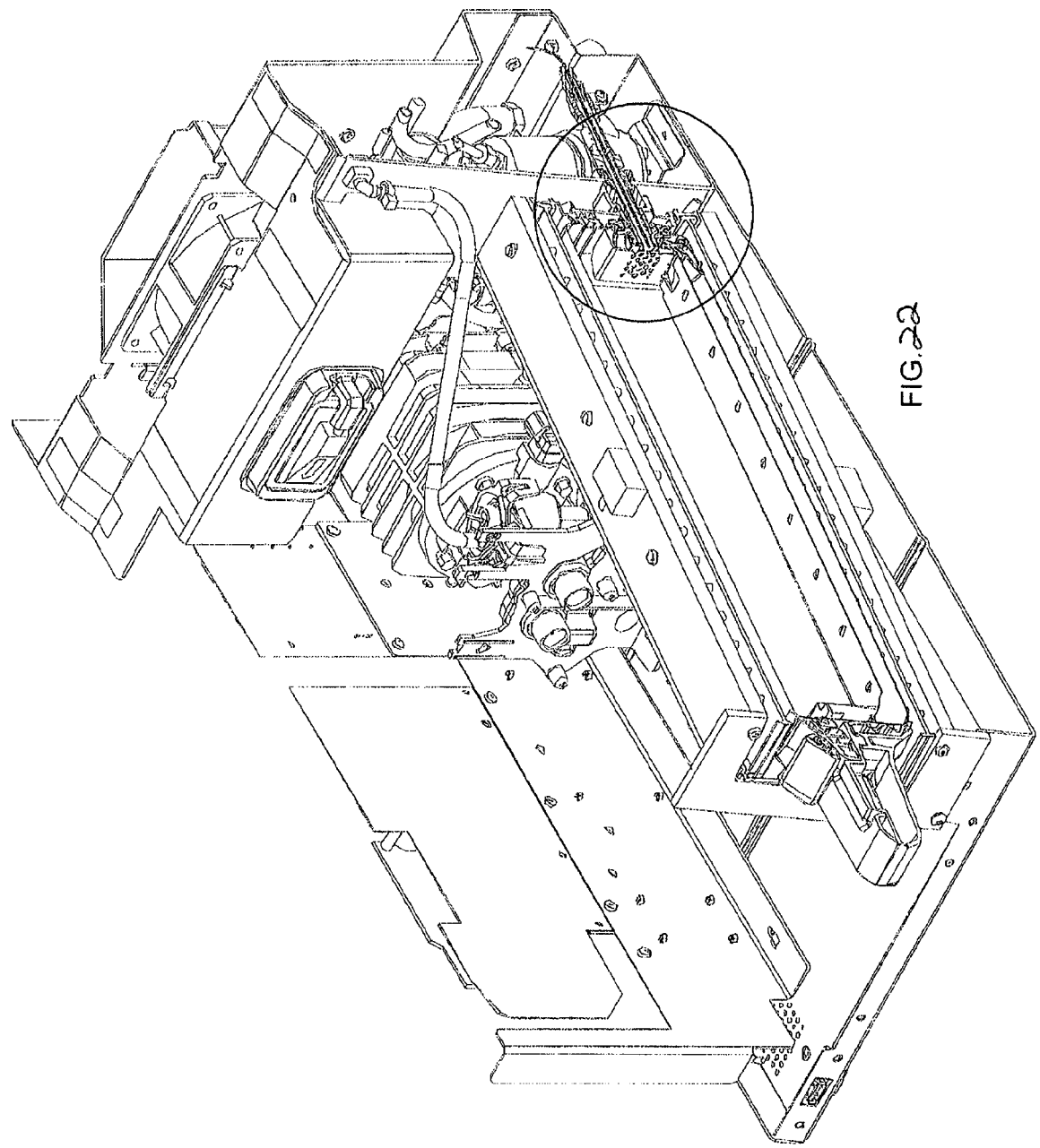
FIG. 22 is vertical sectional view showing the exhaust probe assembly with the cassette and exhaust duct.

As seen in FIGS. 19 and 20, the interprobal space 301 formed between the inner probe 302 and outer probe 304 connects via tube 305 to a first exhaust valve 306 and the inner probe 302 connects via tube 307 to a second exhaust valve 308. The inner probe 302 has a larger cross-sectional area that enables effective mass flow of exhaust steam out of the chamber 12 during the superheated steam drying phase.

Figure 23:
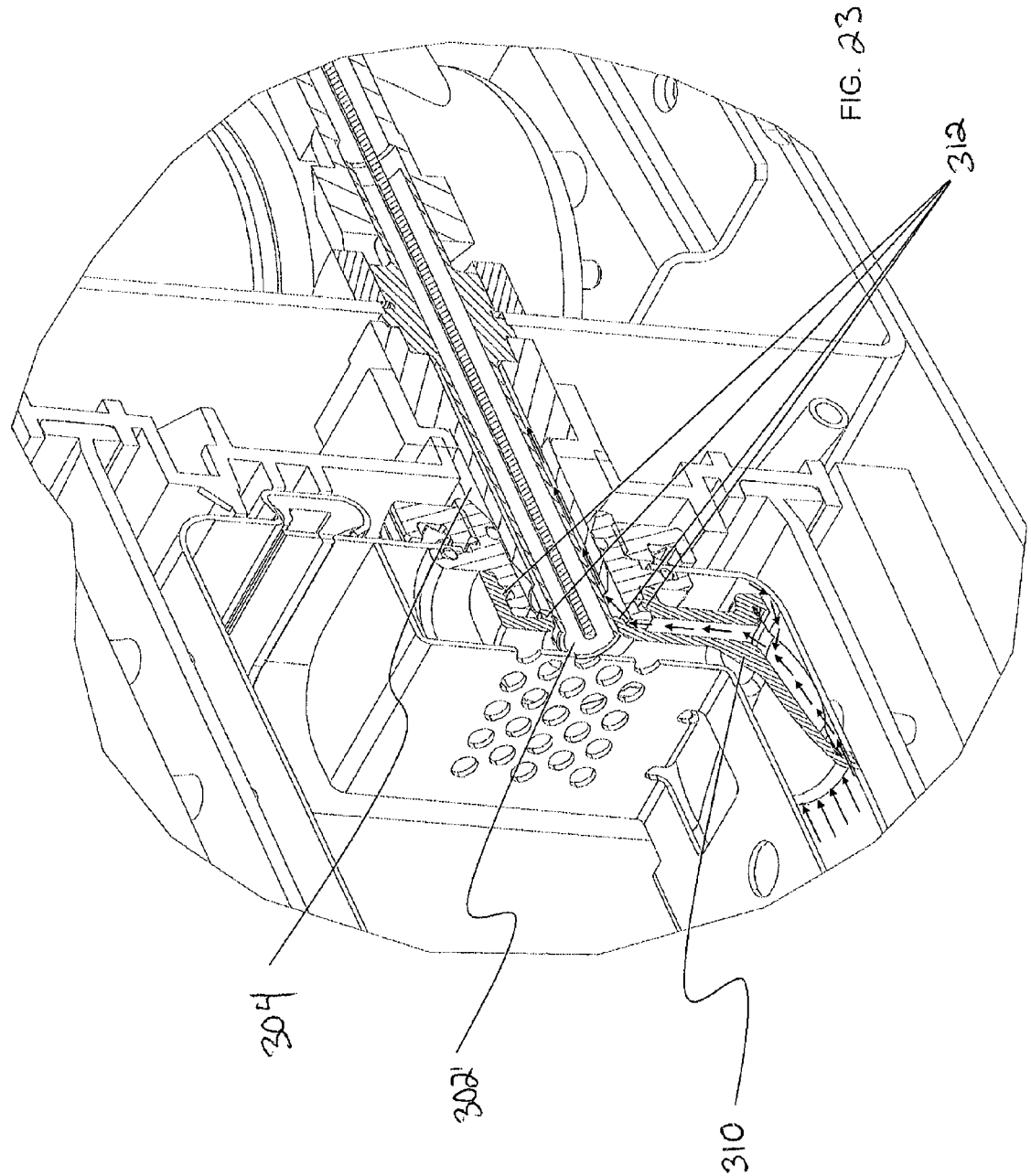
FIG. 23 is a detailed sectional view of the exhaust probe assembly showing the condensate path through the exhaust duct.

The interprobal space 301 formed between the inner and outer probes is sealably isolated from the inner probe opening. This creates a single uninterrupted path between the bottom opening of the exhaust duct 310 and the first exhaust valve 306 to allow effective removal of condensate from the bottom of the chamber 12 when the first exhaust valve 306 is opened during the sterilization phase. At the same time, this also provides an unobstructed opening for the inner probe 302 to facilitate mass flow during superheated steam drying. The inner and outer probes are sealably isolated by the exhaust duct seal 312 (FIG. 23).

The inner probe completely surrounds the chamber thermocouple 350 and protects it from potential damage during cassette insertion.

In use, as seen in FIGS. 20 to 23, there are two steam paths defined. Steam path 320 is the condensate/steam exhaust path during the sterilization phase. This is also the path for condensate exhausted via the first exhaust valve 306 from the bottom of the cassette during the drying phase. Steam path 322 is the steam exhaust path via the second exhaust valve 308 during the superheated steam drying phase. The second path 322 is closed during the sterilization phase and the two paths are isolated from one another during both phases.

The concentric probe arrangement thus eliminates one port from the cassette which reduces the potential leakage points and the number of seals and gaskets that need to be maintained in the cassette.

Directional valve 162 may be operated to selectively direct steam from the steam generator 142 to a first inlet port 160 for the step of sterilizing the instruments. Similarly, directional valve 162 may be operated to selectively direct steam from the steam generator 142 to a second inlet port 14 via the superheated steam heater 144 for drying the instruments.

The superheated steam heater 144 may be preheated prior to the drying step and/or prior to the sterilization step in order to speed up the sterilization and drying process. This preheating step may be performed as part of a start-up procedure for the system 140.

As mentioned previously, the above described apparatus, system and method are particularly suitable for the superheated steam drying of pouched/wrapped instruments or loose (un-pouched) instruments. Sterilization pouches which are commonly used in the medical and dental industries are made of plastic-paper, paper-only and/or fabric sterilization wrap. Superheated steam drying is very effective where the pouch material retains moisture.

A further embodiment of the invention, as noted in paragraph 51 above, is illustrated in FIGS. 12 to 17, in which the distribution means 18 comprises a perforated plate placed within the cassette and operating in conjunction with a deflector plate to distribute the superheated steam within the chamber in a most efficient manner possible. The plate may also be used to support the instruments, i.e. the load to be sterilized and dried.

FIGS. 12a and 12b show a perspective view of the chamber 200, shown as a cassette 202 (without the top), having an inlet means 204 and an exhaust means 206 and incorporating a perforated plate 208. This cassette 202 is of similar construction to that previously described and used in applicant's sterilization systems.

Figure 13:
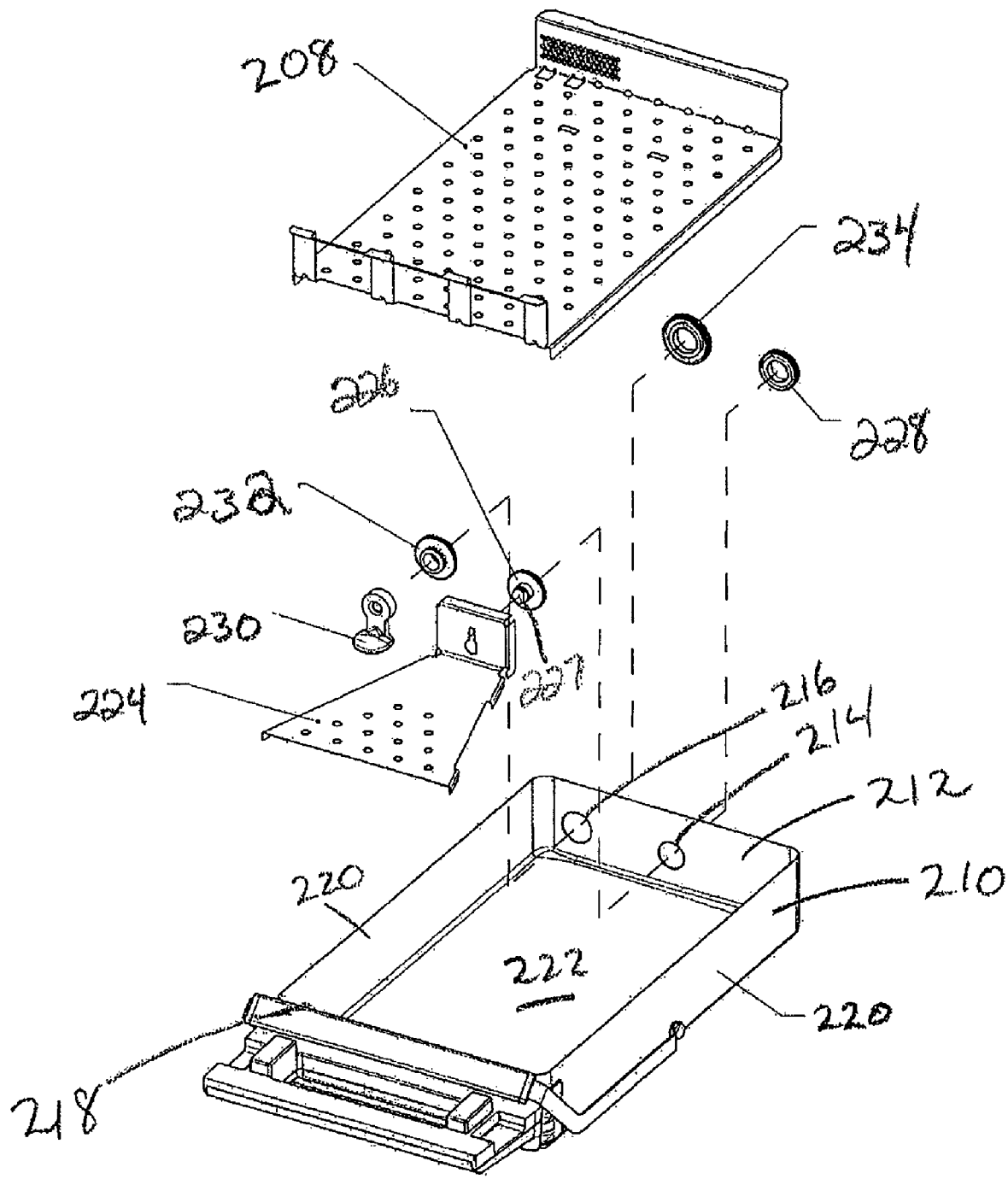
FIG. 13 is an exploded perspective view of a tray and distribution means of the present invention.

FIG. 13 shows an exploded perspective view of the components of this embodiment of the design. The cassette tray 210 has a rear wall 212 with apertures 214, 216 in it. The tray has a front wall 218, side walls 220 and a floor 222, in a conventional design.

This embodiment of the distribution means 18 incorporates the perforated plate 208 which, along with a steam deflector 224 fits within the tray 210. The aperture 214 is configured to operate as part of the inlet means 204 with an inlet port 226, and an inlet port nut 228. The aperture 216 is configured to operate as part of the exhaust means 206 with an exhaust duct 230, an exhaust port 232 and an exhaust port nut 234. The exhaust means 206 may preferably comprise the concentric exhaust probe 300 previously described.

Figure 14A:
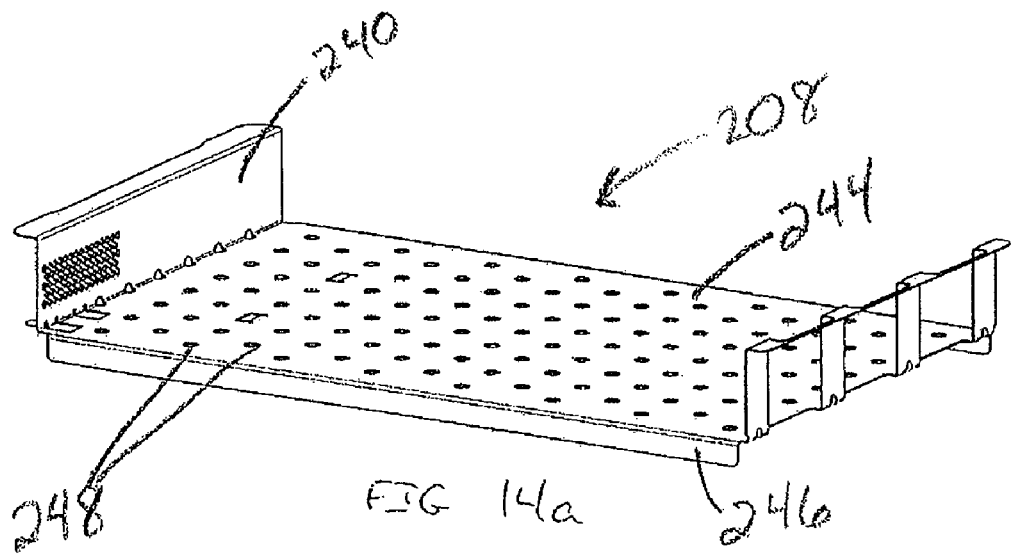
FIGS. 14a and 14b are perspective views of the perforated plate.
Figure 14B:
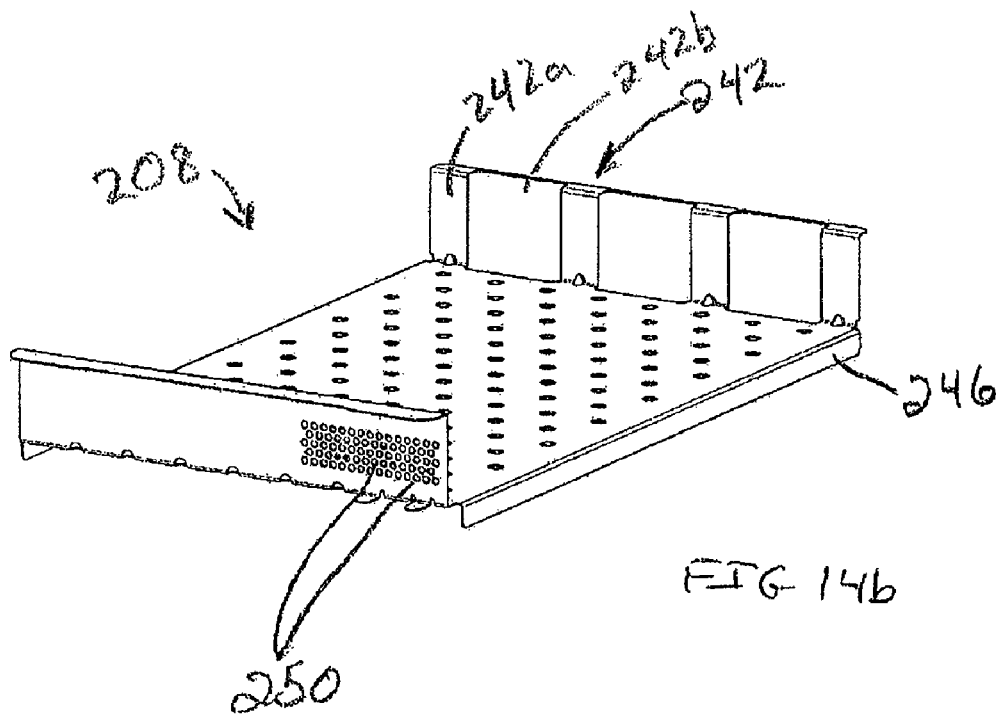

FIGS. 14a and 14b show the perforated plate 208 in greater detail. The plate 208 comprises a rear face 240 and a front face 242, which is shown as a series of supports 242a and openings 242b. The bottom 244 of the plate 208 has a flange 246 on each side running the length of the bottom and extending downwardly from the plane of the bottom 244. As will be described, these flanges create a space between the plate 208 and the cassette floor 222 that allows the flow of steam under the plate 208 from the rear wall 212 toward the front wall 218 of the cassette 202. It should be noted that the plate 208 is not as long as the distance of the bottom 222 as defined between the rear wall 212 and the front wall 218 so that there is a space defined between the front face 242 of the plate 208 and the front wall 218 of the cassette 202 when the plate 208 is in place within the cassette 202.

There is a series of perforations or apertures 248 in the bottom 244 of the plate 208. The rear face 240 also has a series of apertures 250 in one portion thereof, which creates an exhaust opening, sized and positioned to operate as part of the exhaust means 206 during operation.

If the perforated plate 208 is erroneously inserted backwards in the tray 210, a tab on the front of the plate 208 will interfere with the top rear surface of the steam deflector 224, preventing the perforated plate 208 from sitting down in tray 210, and subsequently preventing the cassette lid 290 from closing and the cassette 202 from being inserted into the sterilizer. It is contemplated that further embodiments of the perforated plate/steam deflector assembly could contain more sophisticated error proofing features that will ensure not only that the components are inserted in the correct orientation and that will also prevent operation if the components are not inserted at all.

The perforated plate 208 is preferably made of thermally conductive material. While stainless steel has been used and is suitable due to its durability and consistency of appearance with the cassette 202, other materials, such as aluminum, may also be used, as such materials offer the necessary thermal conduction to provide for faster initial warm-up and hence a faster sterilization cycle and for better heat transfer to the load.

Figure 15A:
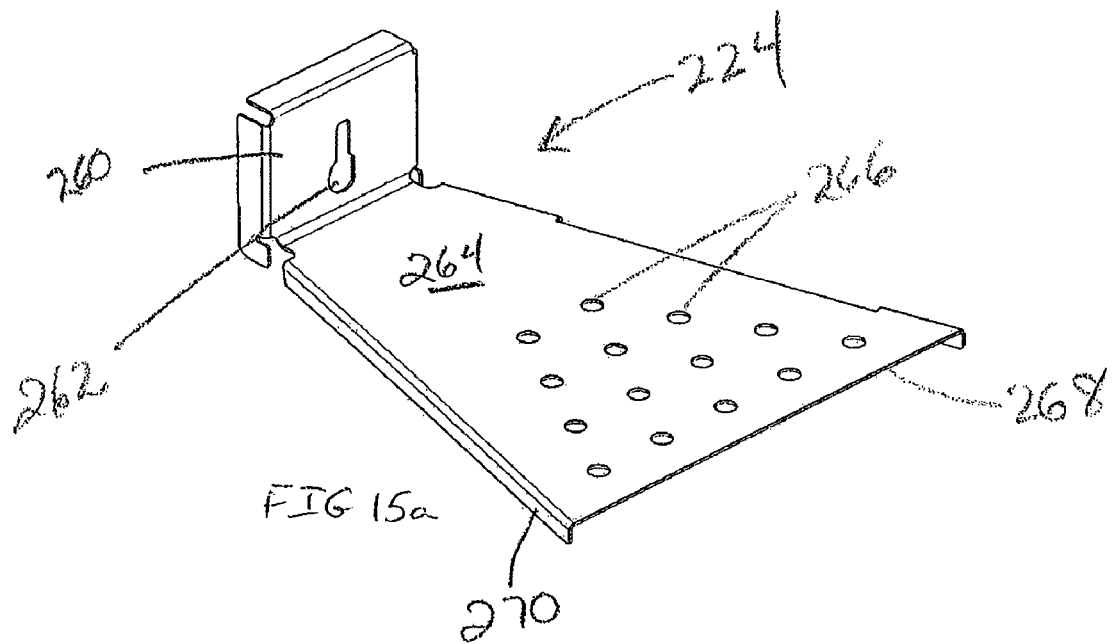
FIGS. 15a and 15b are perspective views of the steam deflector.
Figure 15B:
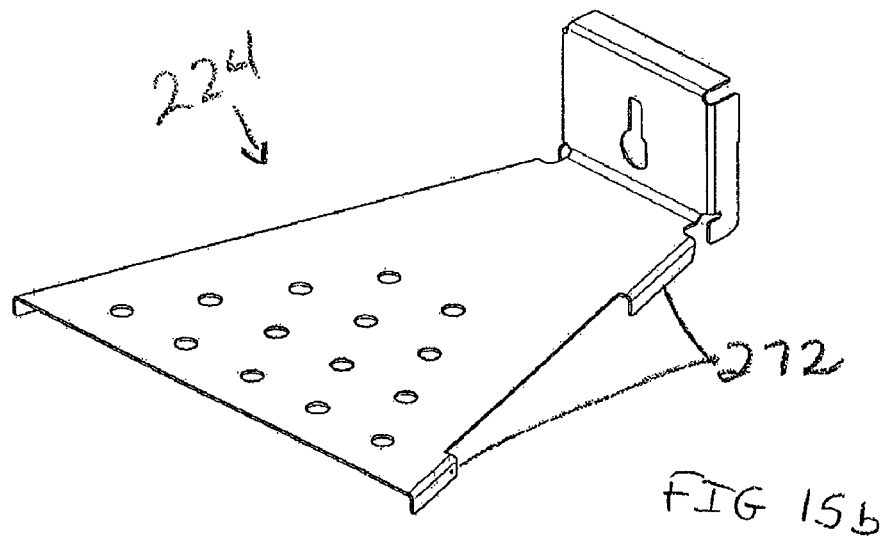

FIGS. 15a and 15b show the steam deflector 224 in greater detail. The deflector 224 comprises an upstanding rear mounting face 260 that includes a mounting keyway 262. The mounting face 260 meets a deflector bottom 264 that flares outwardly from the mounting face 260 and includes a series of perforations or apertures 266 toward the front end 268 of the deflector 224. As illustrated the apertures 266 are only on a portion of the deflector bottom 264 and it will be appreciated that other configurations of the apertures 266 are possible.

The interface between the deflector 224 and the inlet means 204 is important. The deflector 224 is typically removable to allow for regular cleaning of the tray 210 whereas the input port 226 is removably mounted to the rear wall 212 with inlet port nut 228 such as to be removed only for servicing. The inlet port 226 is mounted in the aperture 214 and is allowed to float in 2 dimensions to accommodate positional tolerance variations between the inlet probe and the cassette tray 210. In order to be effective, the steam deflector 224 must sit on the floor 222 of the tray 210, but for error proofing reasons (to ensure that it is always correctly installed), it must also be attached to the inlet port 226. To allow for potential vertical movement of the inlet port 226, a protrusion 227 on the port 226 is engaged in the slotted mounting keyway 262 in the deflector 224. Both the protrusion 227 and the lower portion of the keyway 262 are D-shaped to ensure proper orientation of the port 226. This allows proper orientation and allows the port 226 to effectively float up and down, without lifting the deflector 224 relative to the tray floor 222.

The deflector 224 also includes flanges 270,272 that extend downwardly from the side of the bottom 264. The flange 270 is shown as a continuous flange extending almost the entire length of the deflector bottom 264 and is designed to be on the exhaust side of the deflector 224 when in place within the cassette 202 during operation. The flange 272 is actually a series of tabs (illustrated as two tabs but not limited to that number) spaced along the length of the side of the deflector bottom 264 and designed to be on the input side of the deflector 224 when in place within the cassette 202 during operation. This space between the tabs permits the egress of some of the entering steam to that portion of the cassette tray 210 opposite the exhaust port 232 that is typically otherwise a cold spot.

The flanges 270, 272 create a space between the deflector bottom 264 and the cassette floor 222 to allow for the flow of superheated steam under the deflector toward the front wall 218 of the cassette 202. The flanges 270,272 are not as high as the flanges 246 on the plate 208 thereby creating a separation between the plate 208 and the deflector 224 in use. Radiated heat from the steam deflector 224 to the perforated plate 208 is a prominent mechanism of heat transfer. Therefore, the temperature of the perforated plate 208 is very sensitive to the proximity of the steam deflector 224, and if a minimum separation between the steam deflector 224 and the perforated plate 208 is not maintained, the plate 208 and the local load will heat up beyond the maximum 138 C. allowable.

FIGS. 16 and 17 illustrate the flow of steam within the chamber 200 with the plate 208 and deflector 224 in place, FIG. 17 showing pouched load 280 within the chamber 200.

Superheated steam enters the cassette 202 through the inlet port 226 and is directed by the inlet port 226 and the steam deflector rear mounting face 260 in a downward direction towards the floor 222. It then flows between the steam deflector 224 and the floor 222 forward towards the front wall 218 of the cassette 202. The temperature of the steam entering the cassette 202 is initially greater than 138° C. and is controlled so that at no time does any part of the usable volume of the cassette 202 exceed 138° C.—a processing limitation driven by instrument manufacturers and regulatory bodies. This limitation imposes severe restrictions on the efficacy of using superheated steam as a drying medium. In order to maximize the enthalpy, and hence the drying capacity, of the steam, the temperature of the steam in the usable volume must be as high as possible, without exceeding said restriction of 138° C., and as close to atmospheric pressure as possible.

The majority of the steam passes through the plenum volume created between the perforated plate 208 and the cassette floor 222, heating the perforated plate 208 to a maximum of 138° C., whereupon it passes through the space created between the front face 242 of the plate 208 and the front wall 218 of the cassette 202 and enters the main volume of the cassette 202. This is shown in FIGS. 16 and 17 by the arrows P designating the primary steam path. Depending on how densely the cassette 202 is loaded with instrument pouches 280, some of the superheated steam will also pass through the apertures 248 in the bottom 244 of the perforated plate 208. This is shown in FIGS. 16 and 17 by the arrows S designating the secondary steam path.

The heat in the perforated plate 208 subsequently heats and evaporates liquid moisture contained in the paper side of the pouches 280 (which is facing down) primarily through the mechanism of conduction. Conduction drying is very effective for drying the paper side of the pouches 280 and heating the load. Superheated steam on the other hand is very effective at penetrating the pouches 280, evaporating the moisture within the load and carrying the moisture out of the cassette 202. The resulting, nearly saturated steam, then exits the cassette 202 through the exhaust port 232. The apertures 248 in the perforated plate 208 also act as drainage holes, allowing liquid moisture to fall from the lid 290 of the cassette 202 and the load 280 to the floor 222 of the cassette 202, whereupon it can drain to the back of the cassette 202 and be removed by the exhaust duct 230. The exhaust duct 230 is removable to allow for cleaning. In use (in both the sterilization and drying phases), it is a conduit that defines the path for and allows for the removal of the condensate from the bottom of the tray 210.

It is necessary to remove as much liquid moisture from the bottom 222 of the cassette 202 to prevent the superheated steam energy from being wasted on heating up condensate already separated from the load 280. An effective condensate removal mechanism therefore allows the superheated steam energy to be focused on the load.

There is a tradeoff between having sufficient material in contact with the pouches 280 for conduction drying and sufficient aperture 248 size and density to a) allow some superheated steam to follow the secondary steam path, and b) allow condensed moisture to drain away from the load. The size of the apertures 248 in the perforated plate 208 need to be sufficiently large to overcome the surface tension of the water and allow droplets to fall to the floor 222 of the tray 210, and sufficient in number and density to drain as much condensate as possible. However, contact area between the load 280 and the plate 208 is important for efficient energy transfer; therefore the size and pitch of the apertures 248 cannot be too large. A configuration of staggered apertures provides for better drainage than rows of holes: when the condensate forms on the perforated plate 208, it rolls down towards the back of the plate 240. Staggering the apertures 248 increases the chances of a drop of water draining to the floor 222 of the tray 210 before it hits the back of a pouch 280 and soaks into the paper.

In a different embodiment, the perforated plate 208 would comprise apertures 248 of smaller size than that illustrated and grooves running from end to end. This would increase the thermal mass and contact area between plate 208 and load 280 yet still provide channels to separate and remove the condensed moisture from the load 280.

The cassette 202 is typically tilted at 6° (the higher the tilt, the better) such that the rear of the cassette 202 is lower than the front, promoting the rapid transportation of condensate to the rear of the cassette 202, to be subsequently removed by the exhaust duct 230. There is a variable radius fillet between the floor 222 of the cassette tray 210 and the rear wall 212 which has the effect of channeling the condensate transversely across the rear edge of the tray floor 222 towards the exhaust duct 230 These two mechanisms mean that the sterilizer unit can be placed level in the horizontal plane, and the condensate will migrate to the corner of the tray 210 adjacent to the exhaust port 232 to be expelled by the exhaust duct 230.

As shown by the primary steam path, the steam deflector 224 prevents the hot incoming superheated steam from overheating the local area of the perforated plate 208 by the input means 204, and to prevent the entering steam from prematurely exiting through the exhaust port 232 before it has had a chance to transfer some of its usable energy to the liquid moisture in the cassette 202. The steam then follows the primary path P to the front of the cassette 202 where it travels upwards in the space created between the front wall 218 of the cassette 202 and the front face 242 of the plate 208, towards the lid 290 and then back towards the exhaust means 206. During this flow, the superheated steam evaporates liquid moisture from both the load 280 consisting of the pouches and the instruments, and from the lid 290.

Thus efficient drying of the load 280 is effected by both the radiant and conductive heating from the perforated plate 208, and convection created by the flow of superheated steam along primary path P and secondary path S.

Thus, it is apparent that there has been provided in accordance with the invention an apparatus and method for drying medical or dental instruments and the like using superheated steam and a steam sterilization and superheated steam drying system that fully satisfy the objects, aims and advantages set forth above. While the invention has been described in conjunction with illustrated embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

The invention claimed is:

1. An apparatus for drying instruments using superheated steam, comprising:
    a chamber for receiving the instruments, the chamber having at least one inlet port;
    a steam generation means to generate superheated steam;
    a distribution means connected to the at least one inlet port for distributing superheated steam from the steam generation means, through the inlet port, within the chamber; and
    an exhaust means for purging vaporized moisture from the chamber;
    wherein the exhaust means comprises at least one exhaust port and at least one moisture removal means connected to the at least one exhaust port for removing the vaporized moisture from the chamber; and
    wherein the exhaust port comprises an inner probe and an outer probe concentrically arranged and sealably isolated from one another to define an interprobal space.

2. The apparatus of claim 1 wherein said interprobal space is connected to a first exhaust valve and said inner probe is connected to a second exhaust valve.

3. The apparatus of claim 1 wherein said exhaust port further comprises an exhaust duct to sealably isolate said inner probe from the interprobal space.

4. The apparatus of claim 1 wherein said inner probe cylindrically surrounds a temperature sensor to protect said sensor from damage during the insertion and removal of said chamber.

5. The apparatus of claim 1, wherein the distribution means is a manifold assembly comprising a plurality of distributed steam ports connected by a plurality of interconnected conduits, the plurality of interconnected conduits being connected to the at least one inlet port.

6. The apparatus of claim 1, wherein the distribution means is integrated into a perforated drying rack for supporting and arranging the instruments within the chamber.

7. The apparatus of claim 1, wherein said distribution means comprises a perforated plate configured to sit within the chamber proximate to a bottom of the chamber and a steam deflector means, said steam deflector means is configured to communicate with said inlet port to direct incoming steam downward to said bottom of said chamber, under said perforated plate and forward away from said inlet port toward a front wall of said chamber.

8. The apparatus of claim 7 wherein, in use, said perforated plate is sized such that there is a gap between said perforated plate and a front wall of said chamber when said plate is positioned proximate to a rear wall of said chamber.

9. The apparatus of claim 7 wherein said perforated plate is spaced from said bottom of said chamber a distance greater than a distance between said deflector and said bottom, thereby creating a space between said plate and said deflector when in position within said chamber.

10. In a steam sterilization system for the sterilization of medical or dental instruments using saturated steam, an apparatus for drying the instruments using superheated steam comprising:
    a chamber for receiving the instruments, the chamber having at least one inlet port;
    a steam generation means to generate superheated steam;
    a distribution means connected to the at least one inlet port for distributing superheated steam from the steam generation means, through the inlet port, within the chamber to dry the instruments after the instruments have been sterilized; and
    an exhaust means for purging vaporized moisture from the chamber;
    wherein the exhaust means comprises at least one exhaust port and at least one moisture removal means connected to the at least one exhaust port for removing the vaporized moisture from the chamber; and
    wherein said exhaust port comprises an inner probe and an outer probe concentrically arranged and sealably isolated from one another to define an interprobal space.

11. The system of claim 10 wherein said interprobal space is connected to a first exhaust valve and said inner probe is connected to a second exhaust valve.

12. The system of claim 10 wherein said exhaust port further comprises an exhaust duct to sealably isolate said inner probe from the interprobal space.

13. The system of claim 10, wherein said distribution means comprises a perforated plate configured to sit within the chamber proximate to a bottom of the chamber and a steam deflector means, said steam deflector means is configured to communicate with said inlet port to direct incoming steam downward to said bottom of said chamber, under said perforated plate and forward away from said inlet port toward a front wall of said chamber.

14. The system of claim 10, further comprising a compressor connected to the at least one inlet port for injecting air into the chamber to flush the vaporized moisture from the chamber via the at least one exhaust port.

15. The system of claim 10, wherein the distribution means is a manifold assembly comprising a plurality of distributed steam ports connected by a plurality of interconnected conduits, the plurality of interconnected conduits being connected to the at least one inlet port.

16. The system of claim 15, wherein the chamber comprises a first inlet port for delivering steam to the chamber and a second inlet port for delivering steam to the manifold assembly.

17. The system of claim 16, wherein the steam generation means comprises a steam generator and a superheated steam heater.

18. The system 17 further comprising a directional valve to selectively direct steam from the steam generator to the first inlet port for sterilization of the instruments or from the steam generator to the superheated steam heater and then to the second inlet port via for drying of the instruments.

19. The system of claim 10, wherein the steam generation means comprises a steam generator that selectively produces saturated steam for sterilization of the instruments and superheated steam for drying of the instruments by selectively metering a received amount of water from a reservoir.

* * * * *